(12) United States Patent
Blommel et al.

(10) Patent No.: US 11,952,332 B2
(45) Date of Patent: Apr. 9, 2024

(54) SYSTEMS AND METHODS FOR REFORMING A HEAVY AROMATIC STREAM

(71) Applicant: Virent, Inc., Madison, WI (US)

(72) Inventors: Paul G. Blommel, Oregon, WI (US); Matthew Van Straten, Madison, WI (US); Brice Dally, Madison, WI (US)

(73) Assignee: VIRENT, INC., Madison, WI (US)

( * ) Notice: Subject to any disclaimer, the term of this patent is extended or adjusted under 35 U.S.C. 154(b) by 0 days.

(21) Appl. No.: 17/966,343

(22) Filed: Oct. 14, 2022

(65) Prior Publication Data

US 2023/0122414 A1 Apr. 20, 2023

Related U.S. Application Data

(60) Provisional application No. 63/255,817, filed on Oct. 14, 2021.

(51) Int. Cl.
| | | |
|---|---|---|
| *C07C 4/18* | (2006.01) | |
| *B01D 3/14* | (2006.01) | |
| *C07C 1/22* | (2006.01) | |
| *C07C 5/11* | (2006.01) | |

(Continued)

(52) U.S. Cl.
CPC ............. *C07C 4/18* (2013.01); *B01D 3/143* (2013.01); *C07C 1/22* (2013.01); *C07C 5/11* (2013.01); *C07C 7/005* (2013.01); *C07C 7/04* (2013.01); *C07C 2523/14* (2013.01); *C07C 2523/28* (2013.01); *C07C 2523/30* (2013.01); *C07C 2523/44* (2013.01); *C07C 2529/46* (2013.01)

(58) Field of Classification Search
CPC .... C07C 4/18; C07C 1/22; C07C 5/11; C07C 7/005; C07C 7/04; C07C 2523/14; C07C 2523/28; C07C 2523/30; C07C 2523/44; C07C 2529/46; C07C 7/163; C10G 3/44; C10G 69/04; C10G 69/126; C10G 2300/1096; C10G 2400/30; C10G 45/70; C10G 45/62; B01D 3/143; Y02P 30/20
See application file for complete search history.

(56) References Cited

U.S. PATENT DOCUMENTS

| | | | |
|---|---|---|---|
| 3,702,886 | A | 11/1972 | Argauer et al. |
| 3,709,979 | A | 1/1973 | Chu |

(Continued)

FOREIGN PATENT DOCUMENTS

| | | |
|---|---|---|
| KR | 20200100217 A | 8/2020 |
| WO | 2007075476 A1 | 7/2007 |
| WO | 2008109877 A1 | 9/2008 |

OTHER PUBLICATIONS

International Search Report of related PCT/US2022/046721, dated May 30, 2023, 6 pages.

(Continued)

*Primary Examiner* — Thuan D Dang

(74) *Attorney, Agent, or Firm* — Quarles & Brady LLP

(57) ABSTRACT

Processes, catalysts, and reactor systems for reforming heavy aromatic compounds ($C_{11+}$) into $C_{6-8}$ aromatic compounds are disclosed. Also disclosed are processes, catalysts, and reactor systems for producing aromatic compounds and liquid fuels from oxygenated hydrocarbons, such as carbohydrates, sugars, sugar alcohols, sugar degradation products, and the like.

13 Claims, 4 Drawing Sheets

(51) Int. Cl.
*C07C 7/00* (2006.01)
*C07C 7/04* (2006.01)

(56) References Cited

U.S. PATENT DOCUMENTS

| | | | |
|---|---|---|---|
| 3,786,107 A * | 1/1974 | Kuribayashi et al. ........................ | |
| | | | C10G 29/205 |
| | | | 585/475 |
| 3,832,449 A | 8/1974 | Rosinski et al. | |
| 4,016,245 A | 4/1977 | Plank et al. | |
| 4,076,842 A | 2/1978 | Plank et al. | |
| 4,100,262 A | 7/1978 | Pelrine | |
| 4,107,195 A | 8/1978 | Rollmann | |
| 4,139,600 A | 2/1979 | Rollmann et al. | |
| 4,375,573 A | 3/1983 | Young | |
| 5,019,663 A | 5/1991 | Chou et al. | |
| 6,699,457 B2 | 3/2004 | Cortright et al. | |
| 6,953,873 B2 | 10/2005 | Cortright et al. | |
| 6,964,757 B2 | 11/2005 | Cortright et al. | |
| 6,964,758 B2 | 11/2005 | Cortright et al. | |
| 7,022,888 B2 | 4/2006 | Choudhary et al. | |
| 7,618,612 B2 | 11/2009 | Cortright et al. | |
| 7,767,867 B2 | 8/2010 | Cortright | |
| 7,977,517 B2 | 7/2011 | Cortright et al. | |
| 7,989,664 B2 | 8/2011 | Cortright | |
| 8,017,818 B2 | 9/2011 | Cortright et al. | |
| 8,053,615 B2 | 11/2011 | Cortright et al. | |
| 8,198,486 B2 | 6/2012 | Cortright | |
| 8,231,857 B2 | 7/2012 | Cotright et al. | |
| 8,350,108 B2 | 1/2013 | Cotright et al. | |
| 8,362,307 B2 | 1/2013 | Cortright et al. | |
| 8,367,882 B2 | 2/2013 | Cortright et al. | |
| 8,455,705 B2 | 6/2013 | Cotright et al. | |
| 8,492,595 B2 | 7/2013 | Cortright | |
| 8,933,281 B2 | 1/2015 | Cortright et al. | |
| 8,946,458 B2 | 2/2015 | Blank et al. | |
| 10,005,700 B2 | 6/2018 | Beck et al. | |
| 2008/0216391 A1 | 9/2008 | Cortright et al. | |
| 2009/0211942 A1 | 8/2009 | Cortright et al. | |
| 2009/0253948 A1 | 10/2009 | McCall et al. | |
| 2010/0076233 A1 | 3/2010 | Cortright et al. | |
| 2011/0009614 A1 | 1/2011 | Blommel et al. | |
| 2011/0105814 A1 | 5/2011 | Koivusalmi et al. | |
| 2011/0160482 A1 | 6/2011 | Nagaki et al. | |
| 2011/0245542 A1 | 10/2011 | Cortright et al. | |
| 2011/0306804 A1 | 12/2011 | Cortright | |
| 2013/0185992 A1 | 7/2013 | Cortright et al. | |
| 2013/0289302 A1 | 10/2013 | Cortright | |
| 2014/0275571 A1 | 9/2014 | Beck et al. | |
| 2015/0307412 A1 | 10/2015 | Whitchurch et al. | |
| 2021/0130716 A1 | 5/2021 | Xu et al. | |
| 2021/0253959 A1 | 8/2021 | Koseoglu et al. | |

OTHER PUBLICATIONS

Written Opinion of related PCT/US2022/046721, dated May 30, 2023, 16 pages.

* cited by examiner

SYSTEMS AND METHODS FOR REFORMING A HEAVY AROMATIC STREAM

CROSS-REFERENCE TO RELATED APPLICATIONS

This application claims priority to U.S. Provisional Application No. 63/255,817, filed Oct. 14, 2021, the content of which is hereby incorporated by reference in its entirety.

BACKGROUND

Aromatic hydrocarbons, notably benzene, toluene, and xylenes are important industrial commodities used to produce numerous chemicals, fibers, plastics, and polymers, including styrene, phenol, aniline, polyester, and nylon. Typically, such aromatic hydrocarbons are produced from petroleum feedstocks using well-established refining or chemical processes. More recently, there is a growing interest in providing aromatic hydrocarbons from alternative resources, such as biomass, synthesis gases and natural gas.

Bioreforming processes can produce aromatic hydrocarbons from biomass feedstocks such as cellulose, hemicellulose and lignin. For instance, cellulose and hemicellulose can be used as feedstock for various bioreforming processes, including aqueous phase reforming (APR) and hydrodeoxygenation (HDO)-catalytic reforming processes that, when integrated with hydrogenation, can convert cellulose and hemicellulose into an array of products, including hydrogen, liquid fuels, aromatics, kerosene, diesel fuel, lubricants, and fuel oils, among others. APR and HDO methods and techniques are described in U.S. Pat. Nos. 6,699,457; 6,964,757; 6,964,758; and 7,618,612 (all to Cortright et al., entitled "Low-Temperature Hydrogen Production from Oxygenated Hydrocarbons"); U.S. Pat. No. 6,953,873 (to Cortright et al., entitled "Low-Temperature Hydrocarbon Production from Oxygenated Hydrocarbons"); and U.S. Pat. Nos. 7,767,867 and 7,989,664 and U.S. Application No. 2011/0306804 (all to Cortright, entitled "Methods and Systems for Generating Polyols"). Various APR and HDO methods and techniques are described in U.S. Pat. Nos. 8,053,615; 8,017,818 and 7,977,517 and U.S. patent application Ser. Nos. 13/163,439; 13/171,715; 13/163,142 and 13/157,247 (all to Cortright and Blommel, entitled "Synthesis of Liquid Fuels and Chemicals from Oxygenated Hydrocarbons"); U.S. Patent Application No. 2009/0211942 (to Cortright, and entitled "Catalysts and Methods for Reforming Oxygenated Compounds"); U.S. Patent Application No. 2010/0076233 (to Cortright et al., entitled "Synthesis of Liquid Fuels from Biomass"); International Patent Application No. PCT/US2008/056330 (to Cortright and Blommel, entitled "Synthesis of Liquid Fuels and Chemicals from Oxygenated Hydrocarbons"); and commonly owned co-pending International Patent Application No. PCT/US2006/048030 (to Cortright et al., entitled "Catalyst and Methods for Reforming Oxygenated Compounds"), all of which are incorporated herein by reference.

In some instances, light ends (e.g., $C_{5-}$ compounds) and heavy hydrocarbon products (e.g., $C_{11+}$) represent a significant fraction of the condensate product stream produced by the bioreforming process. However, the product value of these streams is typically lower when compared to other products, such as aromatics (e.g., benzene, toluene, xylenes). Currently, there is a need in the art to reform the light ends and heavy hydrocarbon product streams to increase the product value of the respective stream.

SUMMARY OF THE INVENTION

In one aspect, the present disclosure provides a process for producing and separating aromatic hydrocarbons from a hydrocarbon feed stream. The hydrocarbon feed stream may comprise a plurality of non-aromatic hydrocarbons and aromatic hydrocarbons. The non-aromatic hydrocarbons may include a paraffin, an olefin, a naphthene, or combinations thereof, and the aromatic hydrocarbons may include an aryl, a fused aryl, a polycylic compound, or combinations thereof. The process may include fractionating, using a series of distillation columns, the hydrocarbon feed stream to separate an aromatics product stream and a heavy hydrocarbon stream from the hydrocarbon feed stream. The aromatics product stream may comprise a $C_6$ aromatic, a $C_7$ aromatic, a $C_8$ aromatic, or a combination thereof. The heavy hydrocarbon stream may comprise $C_{11+}$ compounds. The process may further include contacting the heavy hydrocarbon stream with a hydrogenation catalyst in the presence of hydrogen to produce a hydrogenated $C_{11+}$ stream, and contacting the hydrogenated $C_{11+}$ stream with at least one conversion catalyst to dealkylate at least a portion of the $C_{11+}$ compounds to generate a reformate stream. The process may further include feeding the reformate stream to the series of distillation columns.

In some embodiments, the fractionating step of the present process include: fractionating, using a first distillation column, the hydrocarbon feed stream to separate a $C_{5-}$ stream and a $C_{6+}$ stream from the hydrocarbon feed stream; fractionating, using a second distillation column, the $C_{6+}$ stream into the aromatic product stream and a $C_{9+}$ stream, wherein the aromatic product stream comprises $C_{6-8}$ compounds; and fractionating, using a third distillation column, the $C_{9+}$ stream into a $C_{9-10}$ stream and the heavy hydrocarbon stream. In the embodiments, the present process further comprises recycling the $C_{5-}$ stream to the at least one conversion catalyst.

In some embodiments, the fractionating step of the present process include: fractionating, using a first distillation column, the hydrocarbon feed stream to separate a $C_{7-}$ stream and a $C_{8+}$ stream from the hydrocarbon feed stream; fractionating, using a second distillation column, the $C_{8+}$ stream into the aromatic product stream and a $C_{9+}$ stream, wherein the aromatic product stream comprises $C_8$ compounds; and fractionating, using a third distillation column, the $C_{9+}$ stream into a $C_{9-10}$ stream and the heavy hydrocarbon stream. In the embodiments, the present process further comprises recycling the $C_{7-}$ stream to the at least one conversion catalyst. In the embodiments, the present process further comprises recycling the $C_{9-10}$ stream to the at least one conversion catalyst to dealkylate at least a portion of $C_{9-10}$ compounds in the $C_{9-10}$ stream.

In some embodiments, the heavy hydrocarbon stream in the present process comprises at least one polynuclear aromatic (PNA). The conversion of the PNA during hydrogenation can be, for example, at least 70%. In some embodiments, the hydrogenated $C_{11+}$ stream of the present process comprises less than 5 wt % polynuclear aromatic compounds, based on the total weight of the hydrogenated $C_{11+}$ stream.

In some embodiments, the hydrogenated $C_{11+}$ stream comprises tetralins. The hydrogenated $C_{11+}$ stream may comprise a weight fraction of tetralins that is at least 10 wt % greater relative to the weight fraction of tetralins in the heavy hydrocarbon stream comprising $C_{11+}$ compounds, based on the total weight of the respective streams.

In some embodiments, the hydrogenated $C_{11+}$ stream comprises decalins. The hydrogenated $C_{11+}$ stream may comprise a weight fraction of decalins that is at least 10 wt % greater relative to the weight fraction of decalins in the heavy hydrocarbon stream comprising $C_{11+}$ compounds, based on the total weight of the respective streams.

In some embodiments, the present process further comprises, prior to the fractionating step, catalytically reacting a feedstock stream comprising water and oxygenated hydrocarbons in the presence of hydrogen with a deoxygenation catalyst to produce a deoxygenated product stream; and catalytically reacting the deoxygenated product stream with the at least one conversion catalyst to produce the hydrocarbon feed stream.

In another aspect, the present disclosure provides a process, which includes catalytically reacting a feedstock stream comprising water and oxygenated hydrocarbons in the presence of hydrogen with a deoxygenation catalyst to produce a deoxygenated product stream. The process may further include catalytically reacting the deoxygenated product stream with at least one conversion catalyst to produce a condensation product stream comprising non-aromatic hydrocarbons and aromatic hydrocarbons, wherein the non-aromatic hydrocarbons comprise a paraffin, an olefin, a napthene, or combinations thereof, and wherein the aromatic compounds comprise an aryl, a fused aryl, a polycylic compound, or combinations thereof. The process may further include fractionating, using a series of distillation columns, the condensation product stream to separate an aromatics product stream and a heavy hydrocarbon stream from the condensation product stream, wherein the aromatics product stream comprises a $C_6$ aromatic, a $C_7$ aromatic, a $C_8$ aromatic, or a combination thereof, and wherein the heavy hydrocarbon stream comprises $C_{11+}$ compounds. The process may further include recycling at least a portion of the heavy hydrocarbon stream to the deoxygenation catalyst.

In some embodiments, the oxygenated hydrocarbons comprise a monosaccharide, a disaccharide, an oligosaccharide, a polysaccharide, a sugar alcohol, a sugar degradation product, a cellulosic derivative, a hemicellulosic derivative, a lignin derivative, a lingnocellulosic derivative, or a combination thereof.

In some embodiments, the fractionating step comprises: fractionating, using a first distillation column, the condensation product stream to separate a $C_{5-}$ stream and a $C_{6+}$ stream from the condensation product stream; fractionating, using a second distillation column, the $C_{6+}$ stream into the aromatic product stream and a $C_{9+}$ stream, wherein the aromatic product stream comprises $C_{6-8}$ compounds; and fractionating, using a third distillation column, the $C_{9+}$ stream into a $C_{9-10}$ stream and the heavy hydrocarbon stream. In some embodiments, the process may further comprise contacting the $C_{5-}$ stream with the at least one conversion catalyst to convert at least a portion of $C_{5-}$ compounds in the $C_{5-}$ stream into $C_{4+}$ compounds via condensation reactions.

In some embodiments, the fractionating step further comprises: fractionating, using a first distillation column, the condensation stream to separate a $C_{7-}$ stream and a $C_{8+}$ stream from the condensation stream; fractionating, using a second distillation column, the $C_{8+}$ stream into the aromatic product stream and a $C_{9+}$ stream, wherein the aromatic product stream comprises $C_8$ compounds; and fractionating, using a third distillation column, the $C_{9+}$ stream into a $C_{9-10}$ stream and the heavy hydrocarbon stream. In some embodiments, the process may further comprise contacting the $C_{7-}$ stream with the at least one conversion catalyst to convert at least a portion of $C_{7-}$ compounds in the $C_{7-}$ stream into $C_{4+}$ compounds via condensation reactions. In some embodiments, the process may further comprise contacting the $C_{9-10}$ stream with the at least one conversion catalyst to dealkylate at least a portion of $C_{9-10}$ compounds in the $C_{9-10}$ stream.

In some embodiments, the hydrogenation catalyst used in the present disclosure comprises at least one support and at least one metal. The metal may be, for example, Fe, Ru, Co, Pt, Pd, Ni, Re, Cu, alloys thereof, and a combination thereof. The support may comprise, for example, carbon, silica, alumina, zirconia, titania, vanadia, ceria, silica-aluminate, zeolite, kieselguhr, hydroxyapatite, zinc oxide, chromia, or a combination thereof.

In some embodiments, the deoxygenation catalyst used in the present disclosure comprises at least one support and at least one metal. For example, the metal of the deoxygenation catalyst can comprise Pd, W, Mo, Ni, Pt, Ru, Sn, or a combination thereof. For example, the support can comprise zirconia.

In some embodiments, the conversion catalyst used in the present disclosure comprises carbide, nitride, zirconia, alumina, silica, aluminosilicate, phosphate, zeolite, titanium oxide, zinc oxide, vanadium oxide, lanthanum oxide, yttrium oxide, scandium oxide, magnesium oxide, cerium oxide, barium oxide, calcium oxide, hydroxide, heteropolyacid, inorganic acid, acid modified resin, base modified resin, or a combination thereof. For example, the conversion catalyst can comprise a zeolite.

DETAILED DESCRIPTION OF THE INVENTION

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation (e.g., ±10%) as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

Systems and methods that convert biomass or fossil fuel derived oxygenates to hydrocarbons typically produce a distribution of products of varying value. For example, the conversion of oxygenates to aromatics typically results in products including gases, light naphtha, BTX (benzene, toluene, xylene), mid range aromatics (typically $C_9$ and $C_{10}$), and heavier $C_{11+}$ aromatics and hydrocarbons. The value of the liquid products such as gasoline and $C_{11+}$ aromatics may be higher than the gaseous products. In turn, the value of the BTX components is generally higher than the light gases, the mid range, and the heavy aromatics. Depending on the commercial scenario, the value of a xylene product will be higher yet than a mixed BTX product. Accordingly, it is desirable to be able to shift an oxygenate conversion system product profile and overall yield structure from the less valuable to the more valuable products which may be desired for a given scenario.

The present disclosure provides systems and methods for shifting the yield structure of hydrocarbon feeds from non-aromatic compounds (e.g., paraffins, olefins, napthenes), to $C_{6-10}$ aromatic compounds. In some embodiments, the present disclosure provides systems and methods for upgrading light hydrocarbon streams (e.g., $C_5$—) and heavy hydrocarbon streams (e.g., $C_{11+}$) within the hydrocarbon feed to increase the yield of aromatic compounds (e.g., $C_{6-10}$), particularly benzene, toluene, para-xylene, ortho-xylene, and meta-xylene.

Figure 1:
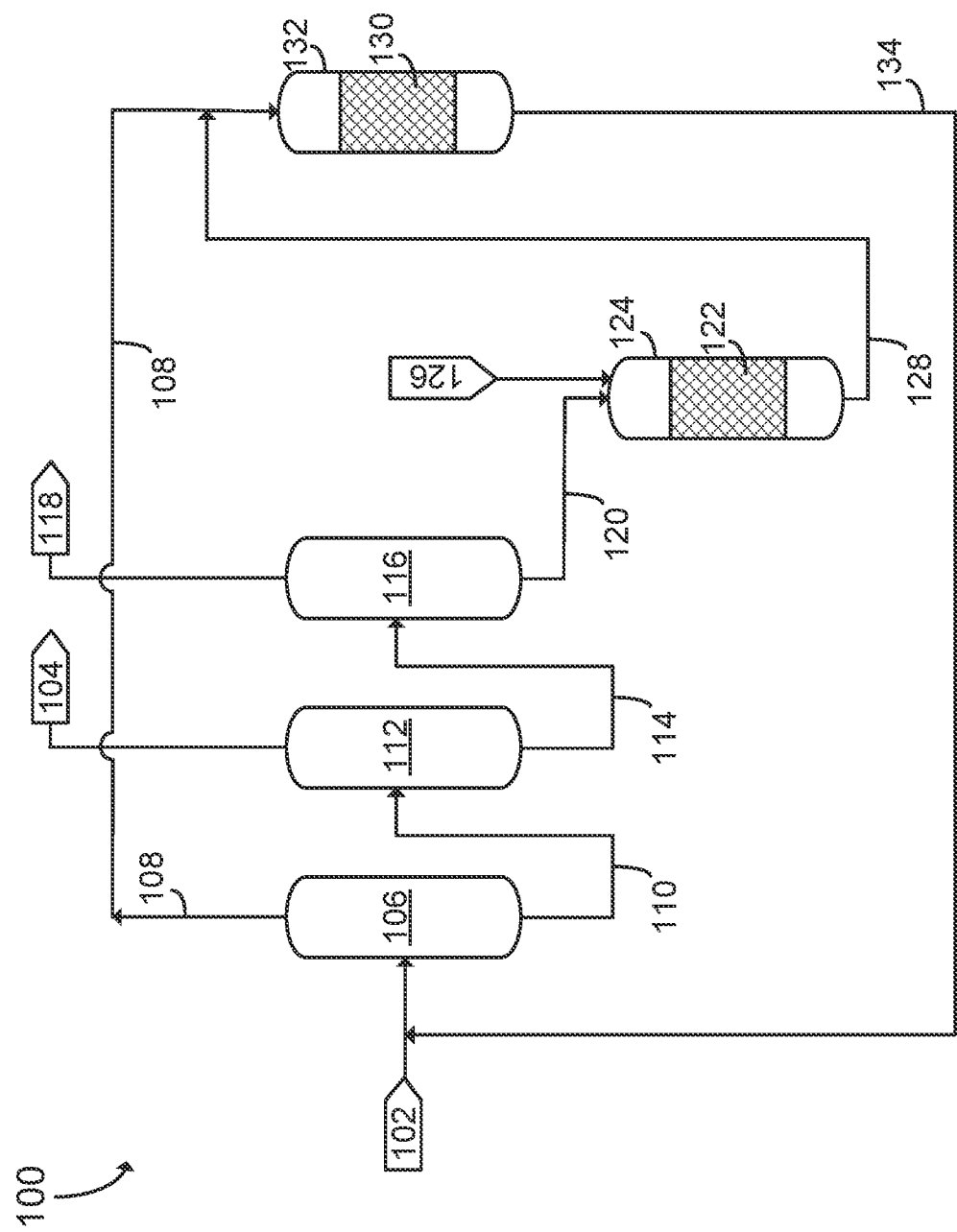
FIG. 1 is an exemplary process for reforming a hydrocarbon feed stream into a $C_{6-8}$ product stream and a $C_{9-10}$ product stream in accordance with some embodiments of the present disclosure.

Referring to FIG. 1, a process 100 for upgrading a hydrocarbon feed stream 102 is illustrated in accordance to some aspects of the present disclosure. In some embodiments, the hydrocarbon feed stream comprises non-aromatic compounds and aromatic compounds, which may be derived from a variety of original sources including, without limitation, biomass derived oxygenates and condensation products, petroleum refining, thermal or catalytic cracking of hydrocarbons, coking of coal, petrochemical conversions, and combinations thereof.

In some embodiments, the hydrocarbon feed stream 102 comprises from 0.1 wt % to 45 wt % non-aromatic hydrocarbons, e.g., paraffins, olefins, naphthenes, or combinations thereof. In some embodiments, the hydrocarbon feed stream comprises at least 0.1 wt % non-aromatic hydrocarbons, or at least 1 wt %, or at least 2 wt % or at least 3 wt %, or at least 4 wt %, or at least 5 wt %, or at least 10 wt %, or at least 15 wt %, or at least 20 wt %, to less than 25 wt %, less than 30 wt %, or less than 35 wt %, or less than 40 wt %, or less than 45 wt %. In some embodiments, the hydrocarbon feed stream comprises $C_{3-30}$ paraffins, $C_{3-30}$ olefins, $C_{5-30}$ naphthenes, or combinations thereof.

As used herein, the term "paraffin" or "alkane" refers to a $C_{3-30}$ saturated straight-chain or branch-chain hydrocarbons. In some embodiments, the paraffins have a general formula of $C_nH_{2n+2}$, where n may range from 3 to 30, from 3 to 25, from 3 to 20, from 3 to 15, from 3 to 10, or from 3 to 6.

As used herein, the term "olefin" or "alkene" refers to a $C_{3-30}$ unsaturated straight-chain or branch-chain hydrocarbon having at least one carbon-carbon double bond. In some embodiments, the olefins have a general formula of $C_nH_{2n}$, where n may range from 3 to 30, from 3 to 25, from 3 to 20, from 3 to 15, from 3 to 10, or from 3 to 6.

Examples of various paraffins and olefins include, without limitation, propane, propene, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

As used herein, the term "naphthenes" or "cycloalkane" refers to a saturated cyclic, bicyclic, or bridged cyclic hydrocarbon group. The saturated cyclic, bicyclic, or bridged cyclic (e.g., adamantane) hydrocarbon group may be substituted with one or more straight-chain or branched-chain alkyl group or alkylene group, e.g., the substituted group(s) may include a straight-chain or branched-chain $C_{1-12}$ alkyl, a straight-chain or branched-chain $C_{3-12}$ alkylene, a straight-chain or branched-chain $C_{1-4}$ alkyl, a straight-chain or branched-chain $C_{3-4}$ alkylene. The naphthene may be mono-substituted or multi-substituted. In some embodiments, the naphthenes have a general formula of $C_nH_{2n}$, where n may range from 5 to 30, from 5 to 25, from 5 to 20, from 5 to 15, from 5 to 10, or from 5 to 6.

Examples of naphthenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, propyl-cyclohexane, butyl-cyclopentane, butyl-cyclohexane, pentyl-cyclopentane, pentyl-cyclohexane, hexyl-cyclopentane, hexyl-cyclohexane, decalin, ethyl-decalin, pentyl-decalin, hexyl-decalin, and isomers thereof. The term "decalins" as used herein includes decalin, substituted decalin compounds (such as ethyl-decalin, pentyl-decalin, or hexyl-decalin), isomers thereof, and any combinations thereof. For example, "decalins" may refer to pure decalin, a pure substituted decalin compound, a mixture of decalin and at least one substituted decalin compound, or a mixture of two or more substituted decalin compounds.

In some embodiments, the hydrocarbon feed stream comprises from 10 wt % to 80 wt % aromatic hydrocarbons, e.g., aryls, fused aryls, polycyclic compounds, or combinations thereof. In some embodiments, the hydrocarbon feed stream comprises at least 10 wt % aromatic hydrocarbons, or at least 10 wt %, or at least 15 wt % or at least 20 wt %, or at least 25 wt %, or at least 30 wt %, or at least 35 wt %, or at least 40 wt %, or at least 45 wt %, to less than 50 wt %, less than 55 wt %, or less than 60 wt %, or less than 65 wt %, or less than 75 wt %, or less than 80 wt % aromatics. In some embodiments, the hydrocarbon feed stream comprises a plurality of $C_{6-30}$ aryls, $C_{12-30}$ fused aryls, $C_{12-30}$ polycylic compounds, or combinations thereof.

As used herein, the term "aryls" refers to an aromatic hydrocarbon in an unsubstituted (e.g., phenyl), mono-substituted, or multi-substituted form. In the case of mono-substituted and multi-substituted compounds, the substituent group may include a branched $C_{3+}$ alkyl, a straight-chain $C_{1+}$ alkyl, a branched-chain $C_{3+}$ alkylene, a straight chain $C_{2+}$ alkylene, or a combination thereof. By way of example, at least one of the substituent groups include a branched-chain $C_{3+}$ alkyl, a straight-chain $C_{1-12}$ alkyl, a branched-chain $C_{3-12}$ alkylene, a straight-chain $C_{2-12}$ alkylene, or a combination thereof. By way of further example, at least one of the substituent groups include a branched $C_{3-4}$ alkyl, a straight chain $C_{1-4}$ alkyl, a branched $C_{3-4}$ alkylene, straight chain $C_{2-4}$ alkylene, or a combination thereof. Examples of various aryls include, without limitation, benzene, toluene, xylene (dimethylbenzene), ethyl benzene, para-xylene, meta-xylene, ortho-xylene, $C_{9+}$ aromatics, butyl benzene, pentyl benzene, hexyl benzene, heptyl benzene, oxtyl benzene, nonyl benzene, decyl benzene, undecyl benzene, and isomers thereof.

As used herein, the term "fused aryl" or "polynuclear aromatic (PNA)" refers to bicyclic and polycyclic aromatic hydrocarbons, in either an unsubstituted, mono-substituted, or multi-substituted form. In the case of mono-substituted and multi-substituted compounds, the substituent group may include a branched-chain $C_{3-12}$ alkyl, a straight-chain $C_{1-12}$ alkyl, a branched-chain $C_{3-12}$ alkylene, a straight-chain $C_{2-12}$ alkylene, a branched-chain $C_{3-4}$ alkyl, a straight-chain $C_{1-4}$ alkyl, a branched-chain $C_{3-4}$ alkylene, straight-chain $C_{2-4}$ alkylene, or a combination thereof. Examples of various fused aryls include, without limitation, naphthalene, anthracene, and isomers thereof.

As used herein, the term "polycyclic compounds" refers to bicyclic and polycyclic hydrocarbons having at least one saturated or partially saturated ring, in either an unsubstituted, mono-substituted, or multi-substituted form. In the case of mono-substituted and multi-substituted compounds, the substituent group may include a branched-chain $C_{3-12}$ alkyl, a straight-chain $C_{1-12}$ alkyl, a branched-chain $C_{3-12}$ alkylene, a straight-chain $C_{2-12}$ alkylene, a branched-chain $C_{3-4}$ alkyl, a straight-chain $C_{1-4}$ alkyl, a branched-chain $C_{3-4}$ alkylene, straight-chain $C_{2-4}$ alkylene, or a combination thereof. Examples of various polycyclic compounds include, without limitation, tetralin (namely, tetrahydronaphthalene), ethyl-tetralin, pentyl-tetralin, hexyl-tetralin, and isomers thereof. The term "tetralins" as used herein includes tetralin, substituted tetralin compounds (such as ethyl-tetralin, pentyl-tetralin, or hexyl-tetralin), isomers thereof, and any combinations thereof. For example, "tetralins" may refer to pure tetralin, a pure substituted tetralin compound, a mixture of tetralin and at least one substituted tetralin compound, or a mixture of two or more substituted tetralin compounds.

The hydrocarbon feed stream 102 may be produced in a variety of ways. In some embodiments, the hydrocarbon feed stream 102 is produced from biomass. The methods, processes, and techniques of converting into a mixture of oxygenated hydrocarbons and condensation products have been well described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); U.S. Pat. Nos. 7,767,867; 7,989,664; 8,198,486; 8,492,595, and U.S. Patent Application Pub. No. 2013/0289302 (all to Cortright, and entitled "Methods and Systems for Generating Polyols"); U.S. Pat. Nos. 8,053,615; 8,017,818; 7,977,517; 8,362,307; 8,367,882; 8,455,705 and U.S. Patent Application Pub. Nos. 2011/0245542 and 2013/0185992 (all to Cortright and Blommel, and entitled "Synthesis of Liquid Fuels and Chemicals from Oxygenated Hydrocarbons"); U.S. Pat. No. 8,231,857 (to Cortright, and entitled "Catalysts and Methods for Reforming Oxygenated Compounds"); U.S. Pat. No. 8,350,108 (to Cortright et al., and entitled "Synthesis of Liquid Fuels from Biomass"); U.S. Patent Application Ser. No. 2011/0160482 (to Nagaki et al., and entitled "Improved Catalysts for Hydrodeoxygenation of Polyols"); U.S. Patent Application Ser. No. 2011/0009614 (to Blommel et al., and entitled "Processes and Reactor Systems for Converting Sugars to Sugar Alcohols"); International Patent Application No. PCT/US2008/056330 (to Cortright and Blommel, and entitled "Synthesis of Liquid Fuels and Chemicals from Oxygenated Hydrocarbons"); commonly owned U.S. Pat. No. 8,231,857 (to Cortright et al., and entitled "Catalyst and Methods for Reforming Oxygenated Compounds"); and U.S. patent application Ser. No. 13/586,499 (to Blank et al., and entitled "Improved Catalysts for Hydrodeoxygenation of Oxygenated Hydrocarbons"); U.S. Pat. No. 10,005,700 (to Beck et al., and entitled "Production of Aromatics from Di- and Polyoxygenates"), all of which are incorporated herein by reference. Hydrocarbon product streams described in the above-mentioned applications and patents may be suitable for use as a hydrocarbon feed stream 102 in accordance with the present application.

Additionally or alternatively, the hydrocarbon feed stream 102 may be derived from petroleum refining, thermal or catalytic cracking of hydrocarbons, coking of coal, or petrochemical conversions. For example, the hydrocarbon feed stream 102 may be derived from appropriate fractions from various petroleum-refinery streams, e.g., as individual components or as certain boiling-range fractions obtained by the selective fractionation and distillation of catalytically cracked or reformed hydrocarbons.

Heavy Aromatics Upgrading (HAU):

Referring back to FIG. 1, a process 100 (and corresponding system) is illustrated for reforming a hydrocarbon feed stream 102 to produce an aromatics product stream 104 comprising $C_{6-8}$ aromatics and hydrocarbons, e.g., benzene, toluene, para-xylene, ortho-xylene, meta-xylene. In some embodiments, the process 100 includes fractionating the hydrocarbon feed stream 102 along with recycled reformate stream 134 in distillation column 106 to separate a $C_{5-}$ stream 108 and a $C_{6+}$ stream 110. As used herein, the term "$C_{n-}$" refers to a hydrocarbon compound having n carbons or fewer in the compound (e.g., 5 or less than 5 carbon atoms), and the term "$C_{11+}$" refers to a hydrocarbon compound having n carbons or greater in the compound (e.g., at least 6 carbons). The $C_{6+}$ stream 110 is fractionated in a second distillation column 112 to separate the $C_{6+}$ stream 110 into a $C_{9+}$ stream 114 and the aromatics product stream 104 comprising $C_{6-8}$ compounds. The $C_{9+}$ stream 114 is fractionated in a third distillation column 116 to separate the $C_{9+}$ stream 114 into a $C_{9-10}$ stream 118 and a $C_{11+}$ stream 120. As described herein, the $C_{11+}$ stream also may be referred to as a heavy hydrocarbon stream, which comprises $C_{11+}$ compounds.

Applicant has found that the $C_{5-}$ stream 108, the $C_{9-10}$ stream 118, and a majority of the $C_{11+}$ stream 120 can be directly reformed over a conversion catalyst 130 to form additional $C_{6-8}$ aromatics via condensation reactions of the $C_{5-}$ stream 108 and dealkylation of the $C_{9-10}$ stream 118 and $C_{11+}$ stream 120. However, it was also found that some PNA compounds in the $C_{11+}$ stream 120, such as naphthalene, are minimally to entirely unreactive over the conversion catalyst 130. It is desirable to convert PNAs into $C_{6-8}$ or $C_{9-10}$ products to maximize yield of the process 100. Applicant further found that polycyclic hydrocarbons (e.g., tetralin) and cycloalkanes (decalin) are reactive across the conversion catalyst 130, and can be converted into the desired $C_{6-8}$ or $C_{9-10}$ products. Aspects of the present disclosure provide methods for converting the PNA compounds (e.g., naphthalene) into reactive polycyclic hydrocarbons (e.g., tetralin) and cycloalkanes (decalin) that can be subsequently reformed over the conversion catalyst 130 to produce an increased concentration of the $C_{6-8}$ aromatics and $C_{9-10}$ compounds.

In some embodiments, the $C_{11+}$ stream 120 is contacted with a hydrogenation catalyst 122 in the presence of hydrogen to produce a hydrogenated $C_{11+}$ stream 128. In some embodiments, the hydrogenation catalyst 122 is disposed in a hydrogenation reactor 124. Hydrogenation reactions can be carried out in any reactor of suitable design, including continuous-flow, batch, semi-batch or multi-system reactors, without limitation as to design, size, geometry, flow rates, etc. The hydrogen reactor 124 can also use a fluidized catalytic bed system, a swing bed system, a fixed bed system, a moving bed system, or a combination of the above. Reactions of the present disclosure are typically practiced using a continuous flow system at steady-state equilibrium. Hydrogen may be provided to the hydrogenation reactor 124 via a hydrogen source 126, which may be a reservoir (e.g., pressurized tank) that contains hydrogen, a recycle stream containing hydrogen from an upstream or downstream process unit, or a combination thereof. The hydrogenation reaction may occur at a temperature from 5° C. to 700° C., from 10° C. to 500° C., from 100° C. to 450° C., or from 200° C. to 400° C. In some embodiments, the hydrogenation reaction may occur at a pressure from 0 psig to 5000 psig, from 500 psig to 3000 psig, from 750 psig to 2000 psig, or from 800 psig to 1400 psig.

In some embodiments, suitable hydrogenation catalysts 122 for the reactor system for the process 100 includes hydrogenation catalysts 122 having one or more active metal and one or more support (e.g., in the hydrogenation reactor 124 as shown in FIG. 1). Suitable active metals include, but are not limited to, Fe, Ru, Co, Pt, Pd, Ni, Re, Cu, alloys thereof, and a combination thereof, either alone or with promoters such as Ag, Au, Cr, Zn, Mn, Mg, Ca, Cr, Sn, Bi, Mo, W, B, P, and alloys or combinations thereof. In some embodiments, the metal of the hydrogenation catalyst is Fe, Ru, Co, Pt, Pd, Ni, Re, Cu, an alloy thereof, or a combination thereof. In some embodiments, the hydrogenation catalyst further comprises at least one promoter. For example, the promoter can be Ag, Au, Cr, Zn, Mn, Mg, Ca, Cr, Sn, Bi, Mo, W, B, P, an alloy thereof, or a combination thereof.

The hydrogenation catalyst may also include any one of several supports, depending on the desired functionality of the catalyst. Exemplary supports include transition metal oxides, an oxide formed from one or more metalloid, and reactive nonmetals (e.g., carbon). Non-limiting examples of supports include, but are not limited to, carbon, silica, alumina, zirconia, titania, vanadia, ceria, silica-aluminate, zeolite, kieselguhr, hydroxyapatite, zinc oxide, chromia, and mixtures thereof.

In some embodiments, the hydrogenated $C_{11+}$ stream 128 comprises less than 10 wt % PNA compounds, based on the total weight of the hydrogenated $C_{11+}$ stream 128. In some embodiments, the hydrogenated $C_{11+}$ stream 128 comprises less than 5 wt %, or less than 4 wt %, or less than 3 wt %, or less than 2 wt %, or less than 1 wt %, or less than 0.5 wt % of PNA compounds, based on the total weight of the hydrogenated $C_{11+}$ stream 128.

In some embodiments, the conversion of the PNA (e.g., naphthalene) compounds in the hydrogenated $C_{11+}$ stream 128 is at least 50%, or at least 55%, or at least 60%, or at least 70%, or at least 75%, or at least 80%, or at least 85%, or at least 90%, or at least 95%. As used herein, conversion of a specific reactant may be calculated by:

$$X_i = 1 - \frac{n_i(t)}{n_i(t=0)}$$

where $X_i$ is conversion and ni is the number of moles of the specific reactant (e.g., naphthalene).

In some embodiments, the weight fraction of tetralins in the hydrogenated $C_{11+}$ stream 128 is at least 10% greater relative to the weight fraction of tetralins in the $C_{11+}$ stream 120, based on the total weight of the respective streams. In some embodiments, the weight fraction of tetralins in the hydrogenated $C_{11+}$ stream 128 is at least 15% greater, or at least 20% greater, or at least 25% greater, or at least 30% greater, or at least 35% greater, to less than 40% greater, or less than 45% greater, or less than 50% greater, relative to the weight fraction of tetralins in the $C_{11+}$ stream 120, based on the total weight of the respective streams.

In some embodiments, the weight fraction of decalins in the hydrogenated $C_{11+}$ stream 128 is at least 10% greater relative to the weight fraction of decalins in the $C_{11+}$ stream 120, based on the total weight of the respective streams. In some embodiments, the weight fraction of decalins in the hydrogenated $C_{11+}$ stream 128 is at least 15% greater, or at least 20% greater, or at least 25% greater, or at least 30% greater, or at least 35% greater, to less than 40% greater, or less than 45% greater, or less than 50% greater, relative to the weight fraction of decalins in the $C_{11+}$ stream 120, based on the total weight of the respective streams.

In some embodiments, the process 100 includes contacting the hydrogenated $C_{11+}$ stream 128 and the $C_{5-}$ stream 108 with a conversion catalyst 130 at a temperature, pressure, and weight hour space velocity effective to induce condensation and dealkylation reactions that produce a reformate stream 134. In particular, the $C_{11+}$ compounds may be dealkylated over the conversion catalyst 130 to produce $C_{10-}$ compounds, and the $C_{5-}$ compounds are converted into $C_{4+}$ compounds via condensation reactions. In this way, the $C_{5-}$ stream 108 and the $C_{11+}$ stream 120 can be reformed to increase the yield of $C_{6-8}$ compounds in the aromatics product stream 104.

Without being limited to any specific theories, it is believed that the conversion catalyst 130 promotes reactions in accordance with the present disclosure that generally comprise a series of steps involving: (a) the dehydration of any oxygenates to alkenes; (b) oligomerization of the alkenes; (c) cracking reactions (e.g., dealkylation); (d) cyclization of larger alkenes to form aromatics; (e) alkane isomerization; (f) hydrogen-transfer reactions to form alkanes. The reactions may also comprise a series of steps involving: (1) aldol condensation to form a β-hydroxyketone or β-hydroxyaldehyde; (2) dehydration of the β-hydroxyketone or β-hydroxyaldehyde to form a conjugated enone; (3) hydrogenation of the conjugated enone to form a ketone or aldehyde, which may participate in further condensation reactions or conversion to an alcohol or hydrocarbon; and (4) hydrogenation of carbonyls to alcohols, or vice-versa. Other condensation reactions may occur in parallel, including aldol condensation, prins reactions, ketonization of acids, and Diels-Alder condensation.

The conversion catalyst 130 will generally be a catalyst capable of forming longer chain compounds by linking two olefins or oxygen containing species, through a new carbon-carbon bond, and converting the resulting compound to a hydrocarbon, alcohol or ketone. The conversion catalyst 130 will also generally be capable of dealkyating heavy $C_{11+}$ aromatics and hydrocarbons. The conversion catalyst may include, without limitation, carbides, nitrides, zirconia, alumina, silica, aluminosilicates, phosphates, zeolites, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The conversion catalyst may include the above alone or in combination with a modifier, such as Ce, La, Y, Sc, P, B, Bi, Li, Na, K, Rb, Cs, Mg, Ca, Sr, Ba, and combinations thereof. The conversion catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality. In some embodiments, the conversion catalyst comprises a metal, which is Cu, Ag, Au, Pt, Ni, Fe, Co, Ru, Zn, Cd, Ga, In, Rh, Pd, Ir, Re, Mn, Cr, Mo, W, Sn, Os, an alloy thereof, or a combination thereof. In some embodiments, the conversion catalyst comprises at least one metal. For example, the conversion catalyst can comprise at least Ni. In some embodiments, the conversion catalyst comprises a modifier, which is Ce, La, Y, Sc, P, B, Bi, Li, Na, K, Rb, Cs, Mg, Ca, Sr, Ba, or a combination thereof.

In certain embodiments the conversion catalyst may include, without limitation, carbides, nitrides, zirconia, alumina, silica, aluminosilicates, phosphates, zeolites (e.g., ZSM-5, ZSM-11, ZSM-12, ZSM-22, ZSM-23, ZSM-35 and ZSM-48), titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The conversion catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

The conversion catalyst 130 may be self-supporting (i.e., the catalyst does not need another material to serve as a support), or may require a separate support suitable for suspending the catalyst in the reactant stream. In certain embodiments the support is selected from the group consisting of alumina, silica, and zirconia. In other embodiments, particularly when the conversion catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 350° C. Other catalyst supports may include those described in further detail below.

In some embodiments, the conversion catalyst comprises a zeolite. The conversion catalyst may include one or more zeolite structures comprising cage-like structures of silica-alumina. Zeolites are crystalline microporous materials with well-defined pore structures. Zeolites contain active sites, usually acid sites, which can be generated in the zeolite framework. The strength and concentration of the active sites can be tailored for particular applications. Examples of suitable zeolites for condensing secondary alcohols and alkanes may comprise aluminosilicates, optionally modified with cations, such as Ga, In, Zn, Mo, and mixtures of such cations, as described, for example, in U.S. Pat. No. 3,702,886, which is incorporated herein by reference. As recognized in the art, the structure of the particular zeolite or zeolites may be altered to provide different amounts of various hydrocarbon species in the product mixture. Depending on the structure of the zeolite catalyst, the product mixture may contain various amounts of aromatic and cyclic hydrocarbons.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. No. 3,702,886; Re. 29,948 (highly siliceous ZSM-5); U.S. Pat. Nos. 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. Nos. 5,019,663 and 7,022,888, also incorporated herein by reference. An exemplary conversion catalyst is a ZSM-5 zeolite modified with Cu, Pd, Ag, Pt, Ru, Re, Ni, Sn, or combinations thereof.

As described in U.S. Pat. No. 7,022,888, the conversion catalyst may be a bifunctional pentasil zeolite catalyst including at least one metallic element from the group of Cu, Ag, Au, Pt, Ni, Fe, Co, Ru, Zn, Cd, In, Rh, Pd, Ir, Re, Mn, Cr, Mo, W, Sn, Os, alloys and combinations thereof, or a modifier from the group of In, Zn, Fe, Mo, Au, Ag, Y, Sc, Ni, P, Ta, lanthanides, and combinations thereof. The zeolite may have strong acidic sites, and may be used with reactant streams containing an oxygenated hydrocarbon at a temperature of below 580° C. The bifunctional pentasil zeolite may have ZSM-5, ZSM-8 or ZSM-11 type crystal structure consisting of a large number of 5-membered oxygen-rings (i.e., pentasil rings). In one embodiment the zeolite will have a ZSM-5 type structure.

Alternatively, solid acid catalysts such as alumina modified with phosphates, chloride, silica, and other acidic oxides may be used in the process. Also, sulfated zirconia, phosphated zirconia, titania zirconia, or tungstated zirconia may provide the necessary acidity. Re and Pt/Re catalysts are also useful for promoting condensation reactions. The Re is sufficiently acidic to promote acid-catalyzed condensation. In certain embodiments, acidity may also be added to activated carbon by the addition of either sulfates or phosphates.

The condensation reactions may occur in a condensation reactor 132. The condensation reactor 132 may have any reactor of suitable design, including continuous-flow, batch, semi-batch or multi-system reactors, without limitation as to design, size, geometry, flow rates, etc. The reactor 132 can also use a fluidized catalytic bed system, a swing bed system, a fixed bed system, a moving bed system, or a combination of the above. Reactions of the present disclosure are typically practiced using a continuous flow system at steady-state equilibrium. Hydrogen may be provided to 132, although this is not depicted in FIG. 1.

The specific $C_{4+}$ compounds (such as $C_{6-8}$ aromatic compounds) and $C_{10-}$ compounds (such as $C_{9-10}$ compounds) produced will depend on various factors, including, without limitation, the type of oxygenated compounds in the reactant stream, condensation temperature, condensation pressure, the reactivity of the catalyst, and the flow rate of the reactant stream as it affects the space velocity, GHSV (gas hourly space velocity), LHSV (liquid hourly space velocity), and WHSV (weight hourly space velocity). In certain embodiments, the reactant stream is contacted with the conversion catalyst at a WHSV that is appropriate to produce the desired hydrocarbon products. In one embodiment the WHSV is at least 0.1 grams of reactant per gram catalyst per hour. In another embodiment the WHSV is between 0.1 to 10.0 g/g hr, including a WHSV of 1, 2, 3, 4, 5, 6, 7, 8, 9, 10 g/g hr, and increments between.

In certain embodiments, the condensation reaction is carried in a condensation reactor 132 at a temperature and pressure at which the thermodynamics of the proposed reaction are favorable. The condensation temperature will vary depending upon the specific composition of the oxygenated compounds. The condensation temperature will generally be greater than 80° C., or 100° C., or 125° C., or 150° C., or 175° C., or 200° C., or 225° C., or 250° C., and less than 500° C., or 450° C., or 425° C., or 375° C., or 325° C., or 275° C. For example, the condensation temperature may be between 80° C. to 500° C., or between 125° C. to 450° C., or between 250° C. to 425° C. The condensation pressure will generally be greater than 0 psig, or 10 psig, or 100 psig, or 200 psig, and less than 2000 psig, or 1800 psig or, or 1600 psig, or 1500 psig, or 1400 psig, or 1300 psig, or 1200 psig, or 1100 psig, or 1000 psig, or 900 psig, or 700 psig. For example, the condensation pressure may be greater than 0.1 psig, or between 0 and 1500 psig, or between 0 and 1200 psig.

The condensation reactions of the present disclosure can be used in the production of $C_{4-30}$ non-aromatic hydrocarbons and $C_{6-30}$ aromatic hydrocarbons, e.g., straight-chain or branched-chain $C_{4-30}$ alkanes, straight-chain or branched-chain $C_{4-30}$ alkenes, $C_{5-30}$ cycloalkanes having optional straight-chain or branched-chain alkyl groups, $C_{5-30}$ cycloalkenes having optional straight-chain or branched-chain alkene groups, $C_{6-30}$ aryls having optional straight-chain or branched-chain alkanes or alkenes, $C_{12-30}$ fused aryls having optional straight-chain or branched-chain alkanes or alkenes, $C_{12-30}$ polycyclic compounds having optional straight-chain or branched-chain alkanes or alkenes, straight-chain or branched-chain $C_{4-30}$ alcohols, straight-chain or branched-chain $C_{4-30}$ ketones, straight-chain or branched-chain $C_{4-30}$ furans and mixtures thereof, with an advantageously high proportion of aryls and a low proportion of alkanes.

In some embodiments, the reformate stream 134 produced by the conversion catalyst 130 is recycled to the distillation column 106. The reformate stream 134 may optionally be combined with the hydrocarbon feed stream 102 prior to feeding into the distillation column 106.

By feeding the $C_{5-}$ stream 108 and the hydrogenated $C_{11+}$ stream 128 to the conversion catalyst 130, the process 100 provides advantages of producing a high concentration of $C_{6-10}$ aromatics, with a low concentration of $C_{4+}$ paraffins and PNA compounds. In particular, the use of the above described process 100 results in a $C_{6-10}$ aryl yield greater than or equal to 50% carbon fraction (CF) of the hydrocarbon feed stream 102, a PNA yield less than or equal to 5% CF of the hydrocarbon feed stream 102, and a $C_{4+}$ alkane yield less than or equal to 25% CF of the aqueous feedstock carbon. In certain embodiments, the $C_{6-10}$ aryls yield can be greater than or equal to 55 wt %, greater than or equal to 60% CF, or greater than or equal to 65% CF of the hydrocarbon feed stream 102. In certain embodiments, the PNA yield is less than 5% CF, or less than 4% CF, or less than 3% CF, or less than 2% CF, or less than 1% CF of the hydrocarbon feed stream 102. In certain embodiments, the $C_{4+}$ alkane yield is less than or equal to 25% CF, less than or equal to 20% CF, less than or equal to 15% CF, or less than 10% CF of the hydrocarbon feed stream 102.

As used herein, the term "carbon fraction" and "CF," which may be used interchangeably, can be calculated by dividing the mass of carbon of the component (e.g. mass of carbon in the aryls) by the mass of carbon in the feed and multiplying by 100. Alternatively, the % CF may be reported as percentage of feed carbon, percentage of carbon in, or other similar nomenclature.

Figure 2:
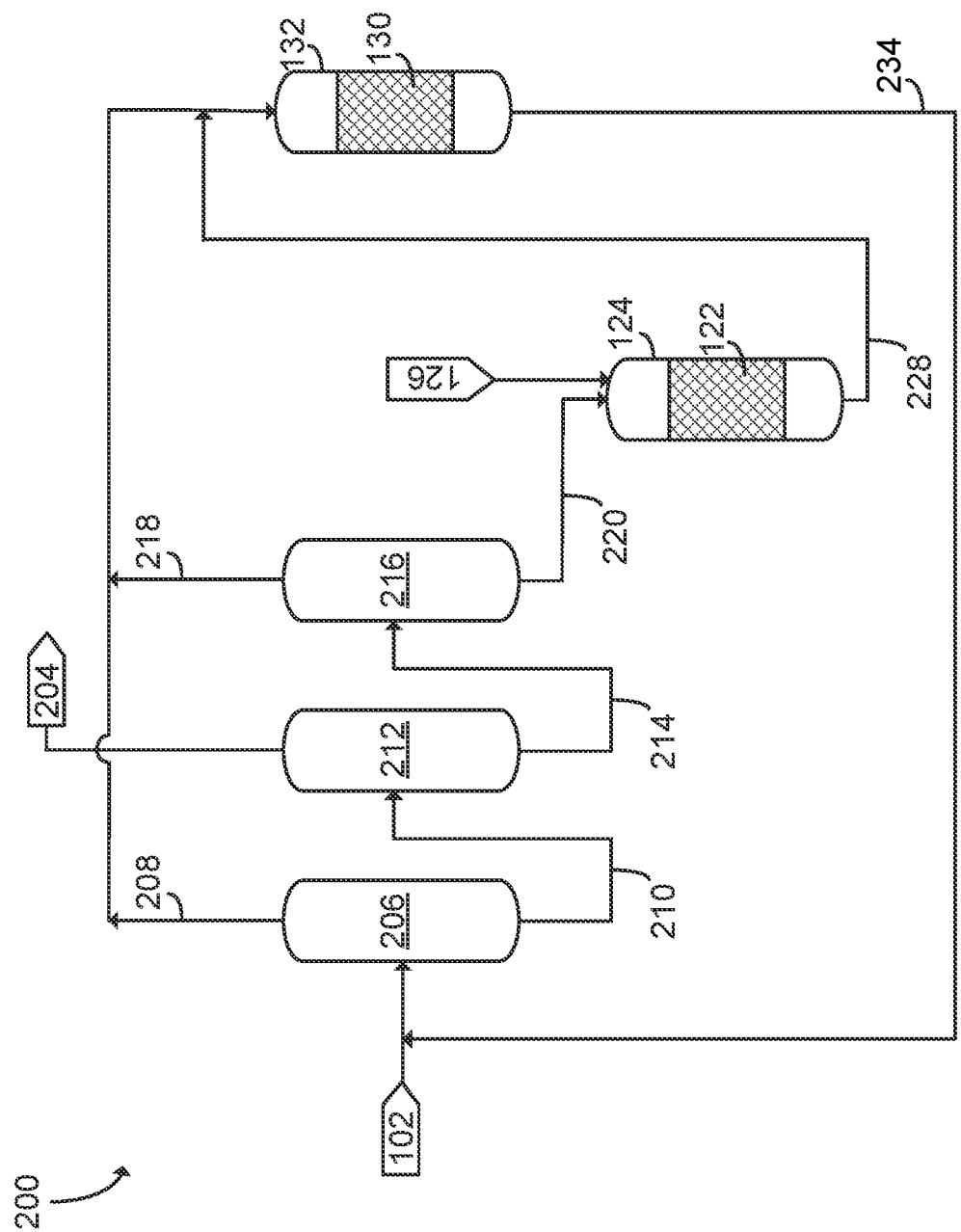
FIG. 2 is an exemplary process for reforming a hydrocarbon feed stream into a $C_8$ product stream in accordance with some embodiments of the present disclosure.

Nothing But Xylenes (NBX):

Referring to FIG. 2, a process 200 is illustrated for reforming a hydrocarbon feed stream 102 to produce an aromatics product stream 204 comprising $C_8$ aromatics and hydrocarbons, e.g., para-xylene, ortho-xylene and meta-xylene, as well as a $C_{9-10}$ product stream 218. Hydrocarbons and aromatics in the $C_{9-10}$ range have applications beyond making other aromatics, such as use in solvents, paints, resins, pesticides, and petroleum drilling. The $C_{9-10}$ product stream 218 may include or be processed to produce products, such as Aromatic 100 solvents (ARO100) or Aromatic 150 solvents (ARO150).

In some embodiments, the process 200 includes fractionating the hydrocarbon feed stream 102 along with recycled reformate stream 234 in distillation column 206 to separate a $C_{7-}$ stream 208 and a $C_{8+}$ stream 210. The $C_{8+}$ stream 210 is fractionated in a second distillation column 212 to separate the $C_{8+}$ stream 210 into a $C_{9+}$ stream 214 and the aromatics product stream 204 comprising $C_8$ compounds. The $C_{9+}$ stream 214 is fractionated in a third distillation column 216 to separate a $C_{9-10}$ stream 218 and a $C_{11+}$ stream 220.

In some embodiments, the $C_{11+}$ stream 220 is contacted with a hydrogenation catalyst 122 in the presence of hydrogen to produce a hydrogenated $C_{11+}$ stream 228. The hydrogenation catalysts 122, hydrogenation reactor 124, and operating conditions described in process 100 are suitable for use in process 200 for generating the hydrogenated $C_{11+}$ stream 228.

In some embodiments, the hydrogenated $C_{11+}$ stream 228 comprises less than 10 wt % PNA compounds, based on the total weight of the hydrogenated $C_{11+}$ stream 228. In some embodiments, the hydrogenated $C_{11+}$ stream 228 comprises less than 5 wt %, or less than 4 wt %, or less than 3 wt %, or less than 2 wt %, or less than 1 wt %, or less than 0.5 wt % of PNA compounds, based on the total weight of the hydrogenated $C_{11+}$ stream 228.

In some embodiments, the conversion of the PNA (e.g., naphthalene) compounds in the hydrogenated $C_{11+}$ stream 228 is at least 50%, or at least 55%, or at least 60%, or at least 70%, or at least 75%, or at least 80%, or at least 85%, or at least 90%, or at least 95%.

In some embodiments, the weight fraction of tetralins in the hydrogenated $C_{11+}$ stream 228 is at least 10% greater relative to the weight fraction of tetralins in the $C_{11+}$ stream 220, based on the total weight of the respective streams. In some embodiments, the weight fraction of tetralins in the hydrogenated $C_{11+}$ stream 228 is at least 15% greater, or at least 20% greater, or at least 25% greater, or at least 30% greater, or at least 35% greater, to less than 40% greater, or less than 45% greater, or less than 50% greater, relative to the weight fraction of tetralins in the $C_{11+}$ stream 220, based on the total weight of the respective streams.

In some embodiments, the weight fraction of decalins in the hydrogenated $C_{11+}$ stream 228 is at least 10% greater relative to the weight fraction of decalins in the $C_{11+}$ stream 220, based on the total weight of the respective streams. In some embodiments, the weight fraction of decalins in the hydrogenated $C_{11+}$ stream 228 is at least 15% greater, or at least 20% greater, or at least 25% greater, or at least 30% greater, or at least 35% greater, to less than 40% greater, or less than 45% greater, or less than 50% greater, relative to the weight fraction of decalins in the $C_{11+}$ stream 220, based on the total weight of the respective streams.

In some embodiments, the process 200 includes contacting the hydrogenated $C_{11+}$ stream 228, the $C_{7-}$ stream 208, and the $C_{9-10}$ stream 218 with a conversion catalyst 130 at a temperature, pressure, and weight hour space velocity effective to induce condensation and dealkylation reactions that produce a reformate stream 134. In particular, the $C_{11}+$ and $C_{9-10}$ compounds may be dealkylated over the conversion catalyst 130 to produce $C_{10-}$ compounds, and the $C_{7-}$ compounds are converted into $C_{4+}$ compounds via condensation reactions. In this way, the $C_{7-}$ stream 208, the $C_{9-10}$ stream 218, and the $C_{11+}$ stream 220 can be reformed to increase the yield of $C_8$ compounds in the aromatics product stream 204. The conversion catalysts 130, condensation reactor 132, and operating conditions described in process 100 are suitable for use in process 200 for generating the reformate stream 234.

In some embodiments, the reformate stream 234 produced by the conversion catalyst 130 is recycled to the distillation column 206. The reformate stream 234 may optionally be combined with the hydrocarbon feed stream 102 prior to feeding into the distillation column 206.

By feeding the hydrogenated $C_{11+}$ stream 228, the $C_{7-}$ stream 208, and the $C_{9-10}$ stream 218 to the conversion catalyst 130, the process 200 provides advantages of producing a high concentration of $C_8$ aromatics, with a low concentration of $C_{4+}$ paraffins and PNA compounds. In particular, the use of the above described process 200 results in a $C_8$ aryl yield greater than or equal to 35% carbon fraction (CF) of the hydrocarbon feed stream 102, a PNA yield less than or equal to 5% CF of the hydrocarbon feed stream 102, and a $C_{4+}$ alkane yield less than or equal to 35% CF of the aqueous feedstock carbon. In certain embodiments, the $C_8$ aryls yield can be greater than or equal to 40 wt %, greater than or equal to 45% CF, to greater than or equal to 50% CF, or greater than or equal to 60% CF of the hydrocarbon feed stream 102. In certain embodiments, the PNA yield is less than 5% CF, or less than 4% CF, or less than 3% CF, or less than 2% CF, or less than 1% CF of the hydrocarbon feed stream 102. In certain embodiments, the $C_{4+}$ alkane yield is less than or equal to 30% CF, less than or equal to 25% CF, or less than or equal to 20% CF of the hydrocarbon feed stream 102.

Figure 3:
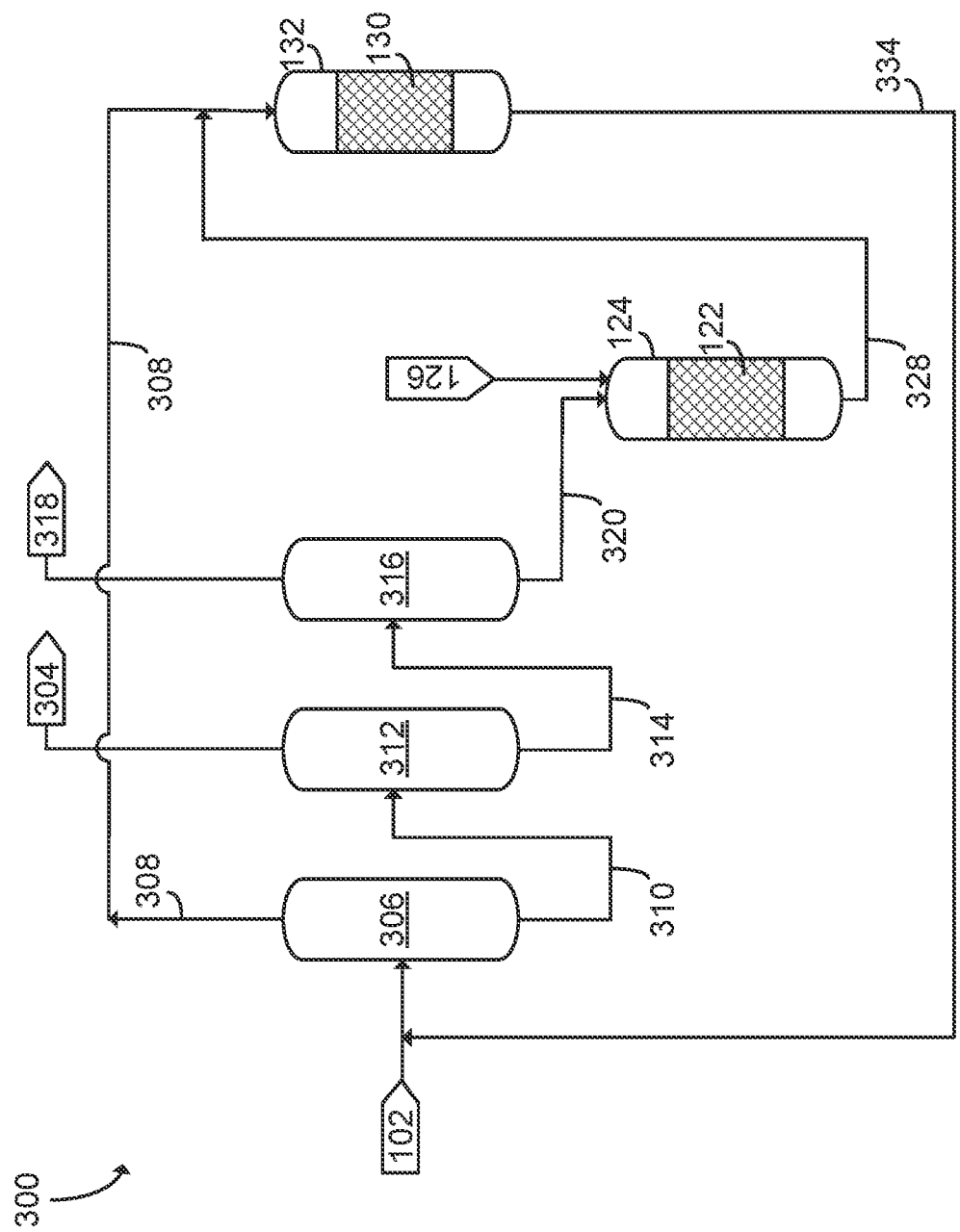
FIG. 3 is an exemplary process for reforming a hydrocarbon feed stream into a $C_8$ product stream and a $C_{9-10}$ product stream in accordance with some embodiments of the present disclosure.

Xylenes-Synthetic Aromatics Kerosene (Xylenes-SAK):

Referring to FIG. 3, a process 300 is illustrated for reforming a hydrocarbon feed stream 102 to produce an aromatics product stream 304 comprising $C_8$ aromatics and hydrocarbons, e.g., para-xylene, ortho-xylene, and meta-xylene, as well as a $C_{9-10}$ product stream 318.

In some embodiments, the process 300 includes fractionating the hydrocarbon feed stream 102 along with recycled reformate stream 334 in distillation column 306 to separate a $C_{7-}$ stream 308 and a $C_{8+}$ stream 310. The $C_{8+}$ stream 310 is fractionated in a second distillation column 312 to separate the $C_{8+}$ stream 310 into a $C_{9+}$ stream 314 and the aromatics product stream 304 comprising $C_8$ compounds. $C_{9+}$ stream 314 is fractionated in a third distillation column 316 to separate a $C_{9-10}$ stream 318 and a $C_{11+}$ stream 320. The $C_{9-10}$ stream is collected as a product stream 318.

In some embodiments, the $C_{11+}$ stream 320 is contacted with a hydrogenation catalyst 122 in the presence of hydrogen to produce a hydrogenated $C_{11+}$ stream 328. The hydrogenation catalysts 122, hydrogenation reactor 124, and operating conditions described in process 100 are suitable for use in process 300 for generating the hydrogenated $C_{11+}$ stream 328.

In some embodiments, the hydrogenated $C_{11+}$ stream 328 comprises less than 10 wt % PNA compounds, based on the total weight of the hydrogenated $C_{11+}$ stream 328. In some embodiments, the hydrogenated $C_{11+}$ stream 328 comprises less than 5 wt %, or less than 4 wt %, or less than 3 wt %, or less than 2 wt %, or less than 1 wt %, or less than 0.5 wt % of PNA compounds, based on the total weight of the hydrogenated $C_{11+}$ stream 328.

In some embodiments, the conversion of the PNA (e.g., naphthalene) compounds in the hydrogenated $C_{11+}$ stream 328 is at least 50%, or at least 55%, or at least 60%, or at least 70%, or at least 75%, or at least 80%, or at least 85%, or at least 90%, or at least 95%.

In some embodiments, the weight fraction of tetralins in the hydrogenated $C_{11+}$ stream 328 is at least 10% greater relative to the weight fraction of tetralins in the $C_{11+}$ stream 320, based on the total weight of the respective streams. In some embodiments, the weight fraction of tetralins in the hydrogenated $C_{11+}$ stream 328 is at least 15% greater, or at least 20% greater, or at least 25% greater, or at least 30% greater, or at least 35% greater, to less than 40% greater, or less than 45% greater, or less than 50% greater, relative to the weight fraction of tetralins in the $C_{11+}$ stream 320, based on the total weight of the respective streams.

In some embodiments, the weight fraction of decalins in the hydrogenated $C_{11+}$ stream 328 is at least 10% greater relative to the weight fraction of decalins in the $C_{11+}$ stream 320, based on the total weight of the respective streams. In some embodiments, the weight fraction of decalins in the hydrogenated $C_{11+}$ stream 328 is at least 15% greater, or at least 20% greater, or at least 25% greater, or at least 30% greater, or at least 35% greater, to less than 40% greater, or less than 45% greater, or less than 50% greater, relative to the weight fraction of decalins in the $C_{11+}$ stream 320, based on the total weight of the respective streams.

In some embodiments, the process 300 includes contacting the hydrogenated $C_{11+}$ stream 328 and the $C_{7-}$ stream 308 with a conversion catalyst 130 at a temperature, pressure, and weight hour space velocity effective to induce condensation and dealkylation reactions that produce a reformate stream 334. In particular, the $C_{11+}$ compounds may be dealkylated over the conversion catalyst 130 to produce $C_{10-}$ compounds, and the $C_{7-}$ compounds are converted into $C_{4+}$ compounds via condensation reactions. In this way, the $C_{7-}$ stream 308 and the $C_{11+}$ stream 320 can be reformed to increase the yield of $C_8$ compounds in the aromatics product stream 304. The conversion catalysts 130, condensation reactor 132, and operating conditions described in process 100 are suitable for use in process 300 for generating the reformate stream 334.

In some embodiments, the reformate stream 334 produced by the conversion catalyst 130 is recycled to the distillation column 306. The reformate stream 334 may optionally be combined with the hydrocarbon feed stream 102 prior to feeding into the distillation column 106.

By feeding the hydrogenated $C_{11+}$ stream 328 and the $C_{7-}$ stream 308 to the conversion catalyst 130, the process 300 provides advantages of producing a high concentration of $C_{8-10}$ aromatics, with a low concentration of $C_{4+}$ paraffins and PNA compounds. In particular, the use of the above described process 300 results in a $C_{8-10}$ aryl yield greater than or equal to 35% carbon fraction (CF) of the hydrocarbon feed stream 102, a PNA yield less than or equal to 5% CF of the hydrocarbon feed stream 102, and a $C_{4+}$ alkane yield less than or equal to 25% CF of the aqueous feedstock carbon. In certain embodiments, the $C_{8-10}$ aryls yield can be greater than or equal to 40 wt %, greater than or equal to 45% CF, to greater than or equal to 50% CF, or greater than or equal to 60% CF of the hydrocarbon feed stream 102. In certain embodiments, the PNA yield is less than 5% CF, or less than 4% CF, or less than 3% CF, or less than 2% CF, or less than 1% CF of the hydrocarbon feed stream 102. In certain embodiments, the $C_{4+}$ alkane yield is less than or equal to 25% CF, less than or equal to 20% CF, or less than or equal to 15% CF of the hydrocarbon feed stream 102.

Figure 4:
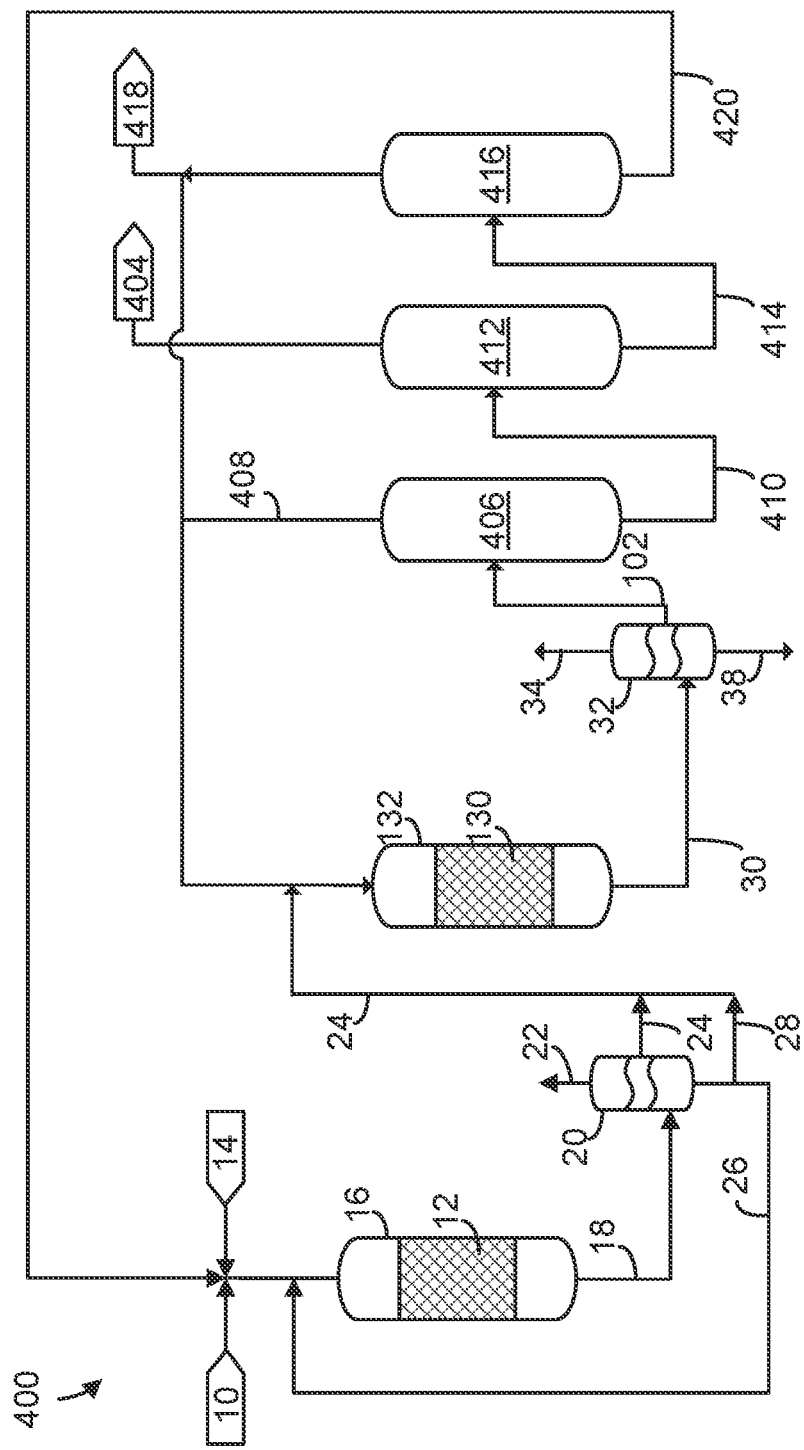
FIG. 4 is an exemplary process for converting oxygenated hydrocarbons to oxygenated compounds

Biomass Feedstock:

Referring to FIG. 4, a process 400 is illustrated for producing a hydrocarbon feed stream 102 that is derived from biomass. The process 400 further includes steps for reforming the hydrocarbon feed stream 102 into an aromatic product stream 404.

As used herein, the term "biomass" refers to, without limitation, organic materials produced by plants (such as leaves, roots, seeds and stalks), and microbial and animal metabolic wastes. Common biomass sources include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, switch grass, alfalfa, prairie bluestream, corn, soybean, and the like.

Various sugar processing methods are well known in the art and commercially practiced at large scale for producing a sugar solution from biomass. For example, in processes using sugar cane, the sugar cane is generally washed, crushed or diffused, and lime clarified to isolate and provide an aqueous biomass-derived intermediate feedstock stream rich in sucrose, fructose, and glucose. In processes using sugar beets, the sugar beets are likewise washed, sliced, extracted, and clarified to isolate and provide an aqueous biomass-derived intermediate feedstock stream in sucrose, fructose, and glucose. For processes involving cereal grains, the cereal grain is cleaned and then processed to provide wet milled starches (corn) or dry milled/ground starches (corn, wheat, barley, sorghum grain). The isolated sugar solution may be adjusted to obtain a desired sugar concentration, e.g., can be concentrated or diluted with water to provide the feedstock solution 10. Generally, a suitable concentration is in the range of about 5% to about 70%, with a range of about 40% to 70% more common in industrial applications.

For a raw feedstock of lignocellulosic biomass, the biomass feed may be deconstructed from complex biopolymers into sugars and soluble oxygenates to form the feedstock solution 10. In one embodiment, the raw lignocellulosic feedstock (such as corn stover) undergoes deconstruction by dilute acid thermochemical pretreatment, pH adjustment by base such as ammonium hydroxide, lime, sodium hydroxide or potassium hydroxide and enzymatic hydrolysis to form soluble sugars. Optional preconversion methods include fractionation in the harvesting of the feedstock, fractionation by sieving, chemical preprocessing to leach out undesired components, fermentative preprocessing such as treatment by white rot fungi, mechanical methods such as steam explosion, torrefaction, or pelleting. Alternate means of deconstruction include thermochemical pretreatment by autohydrolysis (hot water only), alkali (for example, ammonia, sodium hydroxide, potassium hydroxide), oxidation (for example, peroxide, oxygen, air), organosolv (for example, ethanol, acetic acid, catalytically-derived solvents), and ionic liquids. The processing step of lignocellulosic biomass may also include additional processing to provide biomass that has been chopped, shredded, pressed, ground or processed to a size amenable for conversion.

In some embodiments, the feedstock solution 10 may be formed using one or more of the aforementioned processes, and may be derived from one or more of the aforementioned biomass sources. The feedstock solution can be fabricated from biomass by any means now known or developed in the future, or can be simply byproducts of other processes. The feedstock solution also may be referred to as a feedstock stream for the processes as described herein.

In some embodiments, the feedstock solution comprises one or more oxygenated hydrocarbon. The term "oxygenated hydrocarbon" refers to a water-soluble hydrocarbon containing three or more carbon atoms and two or more oxygen atoms, such as carbohydrates (e.g., monosaccharides, disaccharides, oligosaccharides, polysaccharides, and starches), sugars (e.g., glucose, sucrose, xylose, etc.), sugar alcohols (e.g., diols, triols, and polyols), and sugar degradation products (e.g., hydroxymethyl furfural (IMEF), levulinic acid, formic acid, and furfural), each of which is represented herein as $C_{3+}O_{2+}$. As used herein, the term "oxygenated compound" or "oxygenate" refers to a molecule having two or more carbon atoms and one or more oxygen atoms (i.e., $C_{2+}O_{1+}$); the term "monooxygenates" refers to a hydrocarbon molecule containing two or more carbon atoms and one oxygen atom (i.e., $C_{2+}O_1$); the term "dioxygenates" refers to a hydrocarbon molecule containing two or more carbon atoms and two oxygen atoms (i.e., $C_{2+}O_2$); and the term "polyoxygenates" refers to a hydrocarbon molecule containing two or more carbon atoms and three or more oxygen atoms (i.e., $C_{2+}O_{3+}$).

In addition to the oxygenated hydrocarbons, the feedstock may also include lignin, one or more extractives, one or more ash components, or one or more organic species (e.g., lignin derivatives). Extractives include terpenoids, stilbenes, flavonoids, phenolics, aliphatics, lignans, alkanes, proteinaceous materials, amino acids, and other inorganic products. Ash components include Al, Ba, Ca, Fe, K, Mg, Mn, P, S, Si, Zn, etc. Other organic species include 4-ethyl phenol, 4-ethyl-2-methoxy phenol, 2-methoxy-4-propyl phenol, vanillin, 4-propyl syringol, vitamin E, steroids, long chain hydrocarbons, long chain fatty acids, stilbenoids, etc. In some embodiments, the feedstock stream as described herein comprises oxygenated hydrocarbons, and the oxygenated hydrocarbons comprise a monosaccharide, a disaccharide, an oligosaccharide, a polysaccharide, a sugar alcohol, a sugar degradation product, a cellulosic derivative, a hemicellulosic derivative, a lignin derivative, a lingnocellulosic derivative, or a combination thereof.

Referring back to FIG. 4, the feedstock solution 10 is contacted with the deoxygenation catalyst 12 in the presence of hydrogen to produce a deoxygenation product stream 18 comprising a mixture of one or more oxygenate. The hydrogen may be provided from a hydrogen source 14, which could be a reservoir comprising hydrogen (e.g., pressurized tank) or an upstream process unit that produces hydrogen. In some embodiments, the deoxygenation catalyst 12 is disposed in a deoxygenation reactor 16.

The deoxygenation product stream 18 may comprise a $H:C_{eff}$ ratio greater than or equal to 0.5 and less than 2, or from 0.8 to 1.8, or from 1.2 to 1.6, or from 1.2 to 1.6. In some embodiments, the H:C$_{eff}$ ratio is at least 0.5, or at least 0.6, or at least 0.7, or at least 0.8, or at least 0.9, or at least 1, or at least 1.1, or at least 1.2, to less than 1.3, or less than 1.4, or less than 1.5, or less than 1.6, or less than 1.8, or less than 1.9, or less than 2.0.

As used herein, the term "H:C$_{eff}$ ratio" is based on the amount of carbon, oxygen and hydrogen in the feed, and is calculated as follows:

$$H:C_{eff} = \frac{H - 2O}{C},$$

where H represents the number of hydrogen atoms, O represents the number of oxygen atoms, and C represents the number of carbon atoms. Water and molecular hydrogen (diatomic hydrogen, H$_2$) are excluded from the calculation. The H:C$_{eff}$ ratio applies both to individual components and to mixtures of components, but is not valid for components which contain atoms other than carbon, hydrogen, and oxygen. For mixtures, the C, H, and O are summed over all components exclusive of water and molecular hydrogen. The term "hydrogen" refers to any hydrogen atom, while the term "molecular hydrogen" is limited to diatomic hydrogen, H$_2$. In some embodiments, the H:C$_{eff}$ ratio may be controlled or modulated by varying the hydrogenation and hydrodeoxygenation catalyst and operating conditions (e.g., temperature, pressure, WHSV, feed source selection and concentration).

In some embodiments, the deoxygenation product 18 stream includes C$_{1+}$O$_{1-3}$ hydrocarbons, which are compounds having 1 or more carbon atoms and between 1 and 3 oxygen atoms, such as alcohols, ketones, aldehydes, furans, hydroxy carboxylic acids, carboxylic acids, diols, and triols. In some embodiments, the C$_{1+}$O$_{1-3}$ hydrocarbons have from 1 to 6 carbon atoms, or from 2 to 6 carbon atoms, or from 3 to 6 carbon atoms. In addition to C$_{1+}$O$_{1-3}$ hydrocarbons, the deoxygenation product stream 18 may include hydrocarbons having no oxygen elements.

Exemplary alcohols in the deoxygenation product stream 18 may include, without limitation, primary, secondary, linear, branched or cyclic C$_{1+}$ alcohols, such as methanol, ethanol, n-propyl alcohol, isopropyl alcohol, butyl alcohol, isobutyl alcohol, butanol, pentanol, cyclopentanol, hexanol, cyclohexanol, 2-methyl-cyclopentanonol, heptanol, octanol, nonanol, decanol, undecanol, dodecanol, and isomers thereof.

Exemplary ketones may include, without limitation, hydroxyketones, cyclic ketones, diketones, acetone, propanone, 2-oxopropanal, butanone, butane-2,3-dione, 3-hydroxybutan-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, and isomers thereof.

Exemplary aldehydes may include, without limitation, hydroxyaldehydes, acetaldehyde, propionaldehyde, butyraldehyde, pentanal, hexanal, heptanal, octanal, nonal, decanal, undecanal, dodecanal, and isomers thereof.

Exemplary carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid.

Exemplary diols may include, without limitation, ethylene glycol, propylene glycol, 1,3-propanediol, butanediol, pentanediol, hexanediol, heptanediol, octanediol, nonanediol, decanediol, undecanediol, dodecanediol, and isomers thereof.

Exemplary triols may include, without limitation, glycerol, 1,1,1 tris(hydroxymethyl)-ethane (trimethylolethane), trimethylolpropane, hexanetriol, and isomers thereof. Exemplary furans and furfurals include, without limitation, furan, tetrahydrofuran, dihydrofuran, 2-furan methanol, 2-methyl-tetrahydrofuran, 2,5-dimethyl-tetrahydrofuran, 2-methyl furan, 2-ethyl-tetrahydrofuran, 2-ethyl furan, hydroxylmethylfurfural, 3-hydroxytetrahydrofuran, tetrahydro-3-furanol, 2,5-dimethyl furan, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, hydroxymethyltetrahydrofurfural, and isomers thereof.

In some embodiments, the deoxygenation catalyst 12 is composed of a heterogeneous catalyst having one or more materials capable of catalyzing a reaction between hydrogen and a feedstock solution 10 to remove one or more of the oxygen atoms from the feedstock solution to produce one or more oxygenate. In some embodiments, the deoxygenation catalyst 12 is composed of one or more metal adhered to a support and may include, without limitation, Cu, Re, Fe, Ru, Ir, Co, Rh, Pt, Pd, Ni, W, Os, Mo, Ag, Au, alloys and combinations thereof. The deoxygenation catalyst may include these elements alone or in combination with one or more promoters, such as Mn, Cr, Mo, W, V, Nb, Ta, Ti, Zr, Y, La, Sc, Zn, Cd, Ag, Au, Sn, Ge, P, Al, Ga, In, Tl, and combinations thereof. In one embodiment, the deoxygenation catalyst includes Pt, Ru, Cu, Re, Co, Fe, Ni, W or Mo. In yet another embodiment, the deoxygenation catalyst includes Fe or Re and at least one transition metal selected from Ir, Ni, Pd, P, Rh, and Ru. In another embodiment, the catalyst includes Fe, Re and at least Cu or one Group VIIIB transition metal. In some embodiments, the metal of the deoxygenation catalyst comprises Pd, W, Mo, Ni, Pt, Ru, or a combination thereof. In some embodiments, the deoxygenation catalyst comprises a promoter. As an example, the promoter of the deoxygenation catalyst can comprise Sn, W, or a combination thereof. The support may be any one of the supports described herein, including a nitride, carbon, silica, alumina, zirconia, titania, vanadia, ceria, zinc oxide, chromia, boron nitride, heteropolyacids, kieselguhr, hydroxyapatite, and mixtures thereof. In some embodiments, the support comprises zirconia.

The deoxygenation temperature may range from 80° C. to 300° C. In some embodiments, the reaction temperature is between about 120° C. and 600° C., or between about 200° C. and 280° C., or between about 220° C. and 260° C. The deoxygenation pressure may range from 72 psig to 1300 psig. In some embodiments, the deoxygenation pressure ranges from 72 to 1200 psig, or from 145 to 1200 psig, or from 200 to 725 psig, or from 365 to 700 psig, or from 600 to 650 psig.

In some embodiments, the WHSV for the deoxygenation reaction ranges from 0.1 gram of oxygenated hydrocarbon per gram of catalyst per hour (g/g-hr) to 40 g/g-hr. In some embodiments, the WHSV is at least 0.25, at least 0.5, at least 0.75, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, at least 2.5, at least 2.6, at least 2.7, at least 2.8, at least 2.9, at least 3.0, at least 3.1, at least 3.2, at least 3.3, at least 3.4, at least 3.5, at least 3.6, at least 3.7, at least 3.8, at least 3.9, at least 4.0, at least 4.1, at least 4.2, at least 4.3, at least 4.4, at least 4.5, at least 4.6, at least 4.7, at least 4.8, at least 4.9, at least 5.0, to less than 6, less than 7, less than 8, less than 9, less than 10, less than 11, less than 12, less than 13, less than 14, less than 15, less than 20, less than 25, less than 30, less than 35, or less than 40 g/g hr.

In some embodiments, the amount of hydrogen fed to the deoxygenation reactor 16 ranges from 0-2400%, 5-2400%, 10-2400%, 15-2400%, 20-2400%, 25-2400%, 30-2400%, 35-2400%, 40-2400%, 45-2400%, 50-2400%, 55-2400%, 60-2400%, 65-2400%, 70-2400%, 75-2400%, 80-2400%, 85-2400%, 90-2400%, 95-2400%, 98-2400%, 100-2400%, 200-2400%, 300-2400%, 400-2400%, 500-2400%, 600-2400%, 700-2400%, 800-2400%, 900-2400%, 1000-2400%, 1100-2400%, or 1150-2400%, or 1200-2400%, or 1300-2400%, or 1400-2400%, or 1500-2400%, or 1600-2400%, or 1700-2400%, or 1800-2400%, or 1900-2400%, or 2000-2400%, or 2100-2400%, or 2200-2400%, or 2300-2400%, based on the total number of moles of the oxygenated hydrocarbon(s) in the feedstock, including all intervals between. The hydrogen may be external hydrogen or recycled hydrogen. The term "external $H_2$" refers to hydrogen that does not originate from the feedstock solution, but is added to the reactor system from an external source. The term "recycled $H_2$" refers to unconsumed hydrogen, which is collected and then recycled back into the reactor system for further use.

In some embodiments, the product stream 18 is passed through a three-phase separator 20 to separate the product stream 18 into a non-condensed gas stream 22, an organic products stream 24, and an aqueous products stream 26. The non-condensed gas stream 22 may be composed of hydrogen, carbon dioxide, methane, ethane and propane. The non-condensed gasses may be removed and either combusted to create process heat (i.e., heat for driving the reaction in the deoxygenation reactor), or sent to a separation system where hydrogen can be recovered for recycling back to the hydrogen stream 14. The aqueous products stream 26, containing partially deoxygenated hydrocarbons, may be recycled back to the inlet of the deoxygenation reactor 16. An aqueous purge stream 28, including some monooxygenates (e.g., alcohols), can be used to prevent a build-up of water in the reactor system. The aqueous purge stream 28 can be combined with the organic products stream 24 or discarded from the process.

In some embodiments, the organic products stream 24 comprising oxygenates is contacted with a conversion catalyst 130 at a temperature, pressure, and weight hour space velocity effective to induce condensation reactions that convert the oxygenates into a condensate product stream 30 comprising $C_{4+}$ compounds. The $C_{4+}$ compounds may be comprise one or more of $C_{4-30}$ non-aromatic hydrocarbons and $C_{6-30}$ aromatic hydrocarbons, e.g., straight-chain or branched-chain $C_{4-30}$ alkanes, straight-chain or branched-chain $C_{4-30}$ alkenes, $C_{5-30}$ cycloalkanes having optional straight-chain or branched-chain alkyl groups, $C_{5-30}$ cycloalkenes having optional straight-chain or branched-chain alkene groups, $C_{6-30}$ aryls having optional straight-chain or branched-chain alkanes or alkenes, $C_{12-30}$ fused aryls having optional straight-chain or branched-chain alkanes or alkenes, $C_{12-30}$ polycyclic compounds having optional straight-chain or branched-chain alkanes or alkenes, straight-chain or branched-chain $C_{4-30}$ alcohols, straight-chain or branched-chain $C_{4-30}$ ketones, straight-chain or branched-chain $C_{4-30}$ furans and mixtures thereof.

In some embodiments, the condensation product stream 30 may be passed through a three-phase separator 32 to separate the condensation product stream 30 into an acid condensation gas stream 34, an organic stream 102, and an aqueous stream 38. The organic stream 102 and aqueous stream 38 are separated by density difference, while the acid condensation gas stream 34 comprising uncondensed gases is recycled to the condensation reactor 132 to generate additional $C_{4+}$ compounds. In some embodiments, the aqueous stream 38 is discarded from the process, or further processed in downstream process units.

In some embodiments, the organic stream 102 may form or be similar in composition to the hydrocarbon feed stream 102 described in processes 100-300. In some embodiments, the process 400 includes fractionating the organic stream 102 in a first distillation column 406 to separate the organic stream 102 into a first distillate stream 408 and a first bottoms stream 410. In some embodiments the first distillate stream 408 comprises $C_{7-}$ compounds or $C_{5-}$ compounds, and the first bottoms stream 410 comprises $C_{8+}$ compounds or $C_{6+}$ compounds.

The process 400 further includes fractionating the first bottoms stream 410 in a second distillation column 412 to separate the first bottoms stream 410 into a second distillate stream 404 and a second bottoms stream 414. The second distillate stream 404 may be collected as a product stream and comprises either $C_8$ compounds or $C_{6-8}$ compounds. The second bottoms stream 414 comprises $C_{9+}$ compounds. The process 400 further includes fractionating the second bottoms stream 414 in a third distillation column 416 to separate the second bottoms stream 414 into a third distillate stream 418 comprising $C_{9-10}$ compounds and a third bottoms stream 420 comprising $C_{11+}$ compounds.

Rather than hydrogenating the $C_{11+}$ compounds over a hydrogenation catalyst, process 400 includes a step of recycling the third bottoms stream 420 to the deoxygenation catalyst 12. Applicant has surprisingly found that the deoxygenation catalyst 12 can simultaneously dealkylate the $C_{11+}$ compounds from the third bottoms stream 420 and deoxygenate the water soluble sugars and oxygenates in the feedstock solution 10, while maintaining an acceptable conversion.

In some embodiments, the process further includes contacting the first distillate stream 408 comprising $C_{7-}$ compounds or $C_{5-}$ compounds and the third distillate stream 418 comprising $C_{9-10}$ compounds with the conversion catalyst 130 at a temperature, pressure, and weight hour space velocity effective to induce condensation and dealkylation reactions that produce a reformate stream 134 at a temperature, pressure, and weight hour space velocity effective to induce condensation and dealkylation reactions that produce a reformate stream 134. In some embodiments, the third distillate stream 418 comprising $C_{9-10}$ compounds is collected as a product stream, rather than being recycled back to the conversion catalyst 130.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The present invention has been described in terms of one or more preferred embodiments, and it should be appreciated that many equivalents, alternatives, variations, and modifications, aside from those expressly stated, are possible and within the scope of the invention.

EXAMPLES

The following examples will enable one of skill in the art to more readily understand the principles of the present disclosure. The following examples are presented by way of illustration and are not meant to be limiting in any way.

Comparative Example 1: Baseline Configuration with Sorbitol Feed

A feedstock solution composed of 50 wt % sorbitol in water was reacted over a Pd—Mo—Sn—W $ZrO_2$ HDO catalyst to produce a mixture of oxygenates. 140 grams of the HDO catalyst was loaded into two 1" OD Inconel reactors connected in series. Before feed was introduced, the HDO catalyst was reduced in-situ with hydrogen at 400° C. and 1050 psig. The feedstock solution was reacted over the HDO catalyst at 1800 psig and a weight hour space velocity (WHSV) of 0.8 grams of feedstock solution per gram of catalyst per hour. The first HDO reactor had an inlet temperature of 232° C. and an outlet temperature of 254° C. The second HDO reactor had an inlet temperature of 264° C. and an outlet temperature of 295° C. Hydrogen was co-fed to the HDO reactors at a rate of 2550 ml/min. An aqueous recycle of 7.5 g/min from the product HDO product stream was sent back to the HDO inlet.

The mixture of oxygenates produced from the HDO reactors was subsequently reacted over a Ni-modified ZSM-5 conversion catalyst to produce a mixed aromatic feed stream. 165 grams of the Ni-modified ZSM-5 catalyst was loaded into a 1" OD Inconel lead reactor, and 150 grams of Ni-modified ZSM-5 catalyst was loaded into a 1" OD Inconel lag reactor. Regenerations took place daily with reactors swung in the order of regeneration to lag to lead (swing forward). Before feed was introduced, the conversion catalyst was reduced in-situ under nitrogen at 100 psig and 400° C. The mixture of oxygenates were reacted over the conversion catalyst at 100 psig. The lead and lag AC reactors had an inlet temperature of 410° C. and an outlet temperature of 405° C. Hydrogen from the HDO reactors was separated and sent co-fed to the AC reactor. An aqueous recycle of 1 to 3 g/min from the AC product stream was recycled back to the lead AC reactor. A vapor recycle of 3000 mL/min from the AC product stream was recycled back to the AC reactor.

The AC product stream was sent to a distillation column configured to separate the AC product stream into a $C_{6-}$ stream and a $C_{7+}$ stream. The $C_{6-}$ stream was then recycled back to the AC catalyst for further upgrading of the light end products to aromatics. The $C_{7+}$ stream was collected as a product.

TABLE 1

|  | Sorbitol Baseline (% of Feed Carbon) |
|---|---|
| C4− Paraffins | 16.4% |
| C5+ Paraffins | 2.5% |
| C6, C7 Aromatics | 15.0% |
| C8 Aromatics | 22.7% |
| C9 Aromatics | 15.1% |
| C10+ Aromatics | 5.7% |
| PNAs | 7.7% |
| Olefins | 1.2% |
| Naphthenes | 0.7% |
| Oxygenates | 0.6% |
| Coke | 1.2% |
| CO, CO2 | 6.8% |

Four weight checks were performed on all product streams to compile a net yield profile. Table 1 summarizes the carbon yield profile, which is an average of the weight checks.

Inventive Example 1: HAU with Sorbitol Feed

A feedstock solution composed of 50 wt % sorbitol in water was reacted over a Pd—Mo—Sn—W $ZrO_2$ HDO catalyst and a Ni-modified ZSM-5 conversion catalyst using the same reaction conditions outlined in Comparative Example 1.

A first distillation column separated the acid condensation product stream into a $C_{5-}$ stream and a $C_{6+}$ stream. The $C_{5-}$ stream was recycled back to the AC catalyst for further upgrading to produce an increased concentration of aromatics. A second distillation column separated the $C_{6+}$ stream into a $C_{6-8}$ stream and a $C_{9+}$ stream. A third distillation column separated the $C_{9+}$ stream into a $C_{9-10}$ stream and a $C_{11+}$ stream. The $C_{9-10}$ stream was collected as a product stream.

The $C_{11+}$ stream was contacted with a commercially available nickel oxide hydrogenation catalyst (KL6560 available from CRI catalysts having 18% Ni) to produce a hydrogenated $C_{11+}$ stream. 10 grams of the hydrogenation catalyst was loaded into ½" OD Inconel reactor. Before feed was introduced, the hydrogenation catalyst was reduced in-situ with hydrogen at 400° C. and 1050 psig. The $C_{11+}$ steam was reacted over the hydrogenation catalyst at 600 psig. The hydrogenation reactor had an inlet temperature of 170° C. and an outlet temperature of 100° C. Hydrogen was co-fed to the hydrogenation reactor at a rate of 150 mL/min. The hydrogenated $C_{11+}$ stream was recycled back to the AC catalyst for dealkylation.

TABLE 2

| Classification | In (wt %) | Out (wt %) |
|---|---|---|
| C6 Aromatic | 0 | 0 |
| C7 Aromatic | 0 | 0 |
| C8 Aromatic | 0.02 | 0 |
| C9 Aromatic | 1.44 | 1.05 |
| C10 Aromatic | 12.60 | 8.80 |
| C11+ Aromatic | 8.82 | 9.01 |
| PNA | 13.02 | 4.11 |
| Tetralins | 27.24 | 23.38 |
| Decalins | 32.59 | 46.60 |
| Naphthenes | 4.28 | 7.05 |
| Paraffins | 0 | 0 |
| C6− | 0 | 0 |

Table 2 contains the composition of material entering the hydrogenation reactor and the composition of the effluent. As discussed, PNAs (e.g., naphthalene) are minimally reactive over the conversion catalyst, while tetralins and decalins are readily dealkylated into $C_{10-}$ aromatics and hydrocarbons. The hydrogenation catalyst was effective at reducing the concentration of PNAs in the $C_{11+}$ stream from 13.02% to 4.11%, based on a percentage of feed carbon.

TABLE 3

|  | Sorbitol HAU (% of Feed Carbon) | Sorbitol Baseline (% of Feed Carbon) |
|---|---|---|
| C4− Paraffins | 17.0% | 16.4% |
| C5+ Paraffins | 3.6% | 2.5% |
| C6, C7 Aromatics | 16.5% | 15.0% |
| C8 Aromatics | 24.2% | 22.7% |
| C9 Aromatics | 19.0% | 15.1% |
| C10+ Aromatics | 1.8% | 5.7% |
| PNAs | 0.8% | 7.7% |
| Olefins | 1.5% | 1.2% |
| Naphthenes | 3.7% | 0.7% |
| Oxygenates | 0.9% | 0.6% |

TABLE 3-continued

|  | Sorbitol HAU (% of Feed Carbon) | Sorbitol Baseline (% of Feed Carbon) |
|---|---|---|
| Coke | 1.2% | 1.2% |
| CO, CO2 | 4.9% | 6.8% |

Four weight checks were performed on all product streams to compile a net yield profile. The net yield profile was an average of the weight checks. Table 3 summarizes the carbon yield profile for the HAU configuration and compares the carbon yield profile to the baseline configuration. Carbon that was once sequestered by $C_{10+}$ aromatics and PNAs (e.g., napthalenes) was redistributed into high value products including saturated compounds like paraffins and naphthenes, as well as unsaturated compounds like aromatics and olefins.

Comparative Example 2: Baseline Configuration with Conditioned Ethanol Feed

A feedstock solution composed of 41.2 wt % ethyl acetate, 27.7 wt % deionized water, and 31.1 wt % 190 proof ethanol was reacted over a Ni-modified ZSM-5 conversion catalyst to produce a mixed aromatic feed stream. 165 grams of the Ni-modified ZSM-5 catalyst was loaded into a 1" OD Inconel lead reactor, and 150 grams of Ni-modified ZSM-5 catalyst was loaded into a 1"OD Inconel lag reactor. Regenerations took place daily with reactors swung in the order of regeneration to lag to lead (swing forward). Before feed was introduced, the conversion catalyst was reduced in-situ under nitrogen at 100 psig and 400° C. The mixture of oxygenates were reacted over the AC reactors in a lag to lead configuration. The pressure of reaction occurred at 200 psig, and at a WHSV of 0.25 grams of feedstock solution per gram of catalyst per hour. The lag AC reactor had an inlet temperature of 405° C. and an outlet temperature of 435° C. The lead AC reactor had an inlet and outlet temperature of 450° C. Hydrogen was not co-fed to the reactor. An aqueous recycle of approximately 1 g/min from the AC product stream was recycled back to the lead AC reactor. A vapor recycle of 2700 mL/min from the AC product stream was recycled back to the lag AC reactor.

The AC product stream was sent to a distillation column configured to separate the AC product stream into a $C_{6-}$ stream and a $C_{7+}$ stream. The $C_{6-}$ stream was then recycled back to the AC catalyst for further upgrading of the light end products to aromatics. The $C_{7+}$ stream was collected as a product.

TABLE 4

|  | Ethanol Baseline (% of Feed Carbon) |
|---|---|
| C4– Paraffins | 14.4% |
| C5+ Paraffins | 2.0% |
| C6, C7 Aromatics | 7.8% |
| C8 Aromatics | 18.0% |
| C9 Aromatics | 23.5% |
| C10+ Aromatics | 13.8% |
| PNAs | 6.2% |
| Olefins | 4.3% |
| Naphthenes | 0.3% |
| Oxygenates | 0.8% |
| Coke | 1.2% |
| CO, CO2 | 3.1% |

Four weight checks were performed on all product streams to compile a net yield profile. Table 4 summarizes the carbon yield profile, which is an average of the weight checks.

Inventive Example 2: HAU with Conditioned Ethanol Feed 41.2 wt % ethyl acetate, 27.7 wt % deionized water, and 31.1 wt % 190 proof ethanol was reacted over a Ni-modified ZSM-5 conversion catalyst to produce a mixed aromatic feed stream using the same reaction conditions outlined in Comparative Example 2.

A first distillation column separated the acid condensation product stream into a $C_{5-}$ stream and a $C_{6+}$ stream. The $C_{5-}$ stream was recycled back to the AC catalyst for further upgrading to produce an increased concentration of aromatics. A second distillation column separated the $C_{6+}$ stream into a $C_{6-8}$ stream and a $C_{9+}$ stream. A third distillation column separated the $C_{9+}$ stream into a $C_{9-10}$ stream and a $C_{11+}$ stream. The $C_{9-10}$ stream was collected as a product stream.

The $C_{11+}$ stream was contacted with a commercially available nickel oxide hydrogenation catalyst (KL6560 available from CRI catalysts having 18% Ni) to produce a hydrogenated $C_{11+}$ stream. 10 grams of the hydrogenation catalyst was loaded into ½" OD Inconel reactor. Before feed was introduced, the hydrogenation catalyst was reduced in-situ with hydrogen at 400° C. and 1050 psig. The $C_{11+}$ steam was reacted over the hydrogenation catalyst at 600 psig. The hydrogenation reactor had an inlet temperature of 130° C. and an outlet temperature of 105° C. Hydrogen was co-fed to the hydrogenation reactor at a rate of 150 mL/min. The hydrogenated $C_{11+}$ stream was recycled back to the AC catalyst for dealkylation.

TABLE 5

| Classification | In (wt %) | Out (wt %) |
|---|---|---|
| C6 Aromatic | 0.00 | 0.00 |
| C7 Aromatic | 0.00 | 0.00 |
| C8 Aromatic | 0.00 | 0.00 |
| C9 Aromatic | 0.05 | 0.12 |
| C10 Aromatic | 9.11 | 8.08 |
| C11+ Aromatic | 11.25 | 11.38 |
| PNA | 35.59 | 3.89 |
| Tetralins | 31.72 | 45.06 |
| Decalins | 11.36 | 27.05 |
| Naphthenes | 0.92 | 4.41 |
| Paraffins | 0.00 | 0.00 |
| Other C6– | 0.00 | 0.01 |

Table 5 contains the composition of material entering the hydrogenation reactor and the composition of the effluent. The hydrogenation catalyst was effective at reducing the concentration of PNAs in the $C_{11+}$ stream from 13.2% to 4.11%, based on a percentage of feed carbon. The hydrogenation catalyst was also effective at increasing the concentration of tetralins and decalins, which are readily dealkylated over the conversion catalyst.

TABLE 6

|  | Ethanol Baseline (% of Feed Carbon) | Ethanol HAU (% of Feed Carbon) |
|---|---|---|
| C4– Paraffins | 14.4% | 18.6% |
| C5+ Paraffins | 2.0% | 1.9% |
| C6, C7 Aromatics | 7.8% | 8.5% |

TABLE 6-continued

|  | Ethanol Baseline (% of Feed Carbon) | Ethanol HAU (% of Feed Carbon) |
|---|---|---|
| C8 Aromatics | 18.0% | 21.8% |
| C9 Aromatics | 23.5% | 23.5% |
| C10+ Aromatics | 13.8% | 10.1% |
| PNAs | 6.2% | 0.7% |
| Olefins | 4.3% | 4.3% |
| Naphthenes | 0.3% | 0.5% |
| Oxygenates | 0.8% | 0.7% |
| Coke | 1.2% | 1.7% |
| CO, CO2 | 3.1% | 3.7% |

Four weight checks were performed on all product streams to compile a net yield profile. The net yield profile was an average of the weight checks. Table 6 summarizes the carbon yield profile for the HAU configuration and compares the carbon yield profile to the baseline configuration. Carbon that was once sequestered by $C_{10+}$ aromatics and PNAs (e.g., napthalenes) was redistributed into higher value products including saturated compounds like paraffins and naphthenes, as well as unsaturated compounds like aromatics and olefins.

Inventive Example 3: NBX with Conditioned Ethanol Feed 41.2 wt % ethyl acetate, 27.7 wt % deionized water, and 31.1 wt % 190 proof ethanol was reacted over a Ni-modified ZSM-5 conversion catalyst to produce a mixed aromatic feed stream using the same reaction conditions outlined in Comparative Example 2.

A first distillation column separated the acid condensation product stream into a $C_{7-}$ stream and a $C_{8+}$ stream. The $C_{7-}$ stream was then recycled back to the AC catalyst for further upgrading to produce an increased concentration of aromatics. A second distillation column separated the $C_{8+}$ stream into a $C_8$ stream and a $C_{9+}$ stream. A third distillation column separated the $C_{9+}$ stream into a $C_{9-10}$ stream and a $C_{11+}$ stream. The $C_{9-10}$ stream was recycled back to the AC catalyst for dealkylation.

The $C_{11+}$ stream was contacted with a commercially available nickel oxide hydrogenation catalyst (KL6560 available from CRI catalysts having 18% Ni) to produce a hydrogenated $C_{11+}$ stream. 10 grams of the hydrogenation catalyst was loaded into ½" OD Inconel reactor. Before feed was introduced, the hydrogenation catalyst was reduced in-situ with hydrogen at 400° C. and 1050 psig. The $C_{11+}$ steam was reacted over the hydrogenation catalyst at 600 psig. The hydrogenation reactor had an inlet temperature of 130° C. and an outlet temperature of 105° C. Hydrogen was co-fed to the hydrogenation reactor at a rate of 150 mL/min. The hydrogenated $C_{11+}$ stream was recycled back to the AC catalyst for dealkylation. The $C_8$ stream comprising xylenes is collected as the net product stream.

TABLE 7

|  | Hydrotreating In (wt %) | Hydrotreating Out (wt %) |
|---|---|---|
| C6 Aromatic | 0.00 | 0.00 |
| C7 Aromatic | 0.00 | 0.00 |
| C8 Aromatic | 0.02 | 0.00 |
| C9 Aromatic | 1.20 | 0.05 |
| C10 Aromatic | 3.45 | 1.64 |
| C11+ Aromatic | 10.76 | 13.30 |
| PNA | 44.37 | 7.40 |

TABLE 7-continued

|  | Hydrotreating In (wt %) | Hydrotreating Out (wt %) |
|---|---|---|
| Tetralins | 34.02 | 69.35 |
| Decalins | 5.44 | 7.87 |
| Naphthenes | 0.72 | 0.38 |
| Paraffins | 0.00 | 0.00 |
| Other C6− | 0.01 | 0.01 |

Table 7 contains the composition of material entering the hydrogenation reactor and the composition of the effluent. The hydrogenation catalyst was effective at reducing the concentration of PNAs in the $C_{11+}$ stream from 44370 to 7.4%, based on a percentage of feed carbon. The hydrogenation catalyst was also effective at increasing the concentration of tetralins and decalins, which are readily dealkylated over the conversion catalyst.

TABLE 8

|  | Ethanol Baseline (% of Feed Carbon) | Ethanol HAU (% of Feed Carbon) | Ethanol NBX (% of Feed Carbon) |
|---|---|---|---|
| C4− Paraffins | 14.4% | 18.6% | 30.0% |
| C5+ Paraffins | 2.0% | 1.9% | 1.2% |
| C6, C7 Aromatics | 7.8% | 8.5% | 0.9% |
| C8 Aromatics | 18.0% | 21.8% | 47.2% |
| C9 Aromatics | 23.5% | 23.5% | 4.1% |
| C10+ Aromatics | 13.8% | 10.1% | 0.0% |
| PNAs | 6.2% | 0.7% | 0.0% |
| Olefins | 4.3% | 4.3% | 5.1% |
| Naphthenes | 0.3% | 0.5% | 0.1% |
| Oxygenates | 0.8% | 0.7% | 0.7% |
| Coke | 1.2% | 1.7% | 2.9% |
| CO, CO2 | 3.1% | 3.7% | 4.3% |

Four weight checks were performed on all product streams to compile a net yield profile. The net yield profile was an average of the weight checks. Table 8 summarizes the carbon yield profile for the NBX configuration and compares the carbon yield profile to the HAU configuration and the baseline configuration. Carbon that was once sequestered by $C_{10+}$ aromatics and PNAs (e.g., napthalenes) was redistributed into higher value products including saturated compounds like paraffins and naphthenes, as well as unsaturated compounds like aromatics and olefins.

Inventive Example 5: Xylenes-SAK with Conditioned Ethanol Feed 41.2 wt % ethyl acetate, 27.7 wt % deionized water, and 31.1 wt % 190 proof ethanol was reacted over a Ni-modified ZSM-5 conversion catalyst to produce a mixed aromatic feed stream using the same reaction conditions outlined in Comparative Example 2.

A first distillation column separates the acid condensation product stream into a $C_{7-}$ stream and a $C_{8+}$ stream. The $C_{7-}$ stream is then recycled back to the AC catalyst for further upgrading. A second distillation column separates the $C_{8+}$ stream into a $C_8$ stream and a $C_{9+}$ stream. A third distillation column separates the $C_{9+}$ stream into a $C_{9-10}$ stream and a $C_{11+}$ stream. The $C_8$ stream and the $C_{9-10}$ stream are collected as net product streams.

The $C_{11+}$ stream was contacted with a commercially available nickel oxide hydrogenation catalyst (KL6560 available from CRI catalysts having 18% Ni) to produce a hydrogenated $C_{11+}$ stream. 10 grams of the hydrogenation catalyst was loaded into ½" OD Inconel reactor. Before feed was introduced, the hydrogenation catalyst was reduced in-situ with hydrogen at 400° C. and 1050 psig. The $C_{11+}$ steam was reacted over the hydrogenation catalyst at 600 psig. The hydrogenation reactor had an inlet temperature of 130° C. and an outlet temperature of 105° C. Hydrogen was co-fed to the hydrogenation reactor at a rate of 150 mL/min. The hydrogenated $C_{11+}$ stream was recycled back to the AC catalyst for dealkylation.

TABLE 9

| | Ethanol Baseline (% of Feed Carbon) | Ethanol HAU (% of Feed Carbon) | Ethanol NBX (% of Feed Carbon) | Ethanol Xylene-SAK (% of Feed Carbon) |
|---|---|---|---|---|
| C4− Paraffins | 14.4% | 18.6% | 30.0% | 23% |
| C5+ Paraffins | 2.0% | 1.9% | 1.2% | 2% |
| C6, C7 Aromatics | 7.8% | 8.5% | 0.9% | 0.1% |
| C8 Aromatics | 18.0% | 21.8% | 47.2% | 17.5% |
| C9 Aromatics | 23.5% | 23.5% | 4.1% | 25% |
| C10+ Aromatics | 13.8% | 10.1% | 0.0% | 9.5% |
| PNAs | 6.2% | 0.7% | 0.0% | 1.5% |
| Olefins | 4.3% | 4.3% | 5.1% | 5% |
| Naphthenes | 0.3% | 0.5% | 0.1% | 0% |
| Oxygenates | 0.8% | 0.7% | 0.7% | 0.5% |
| Coke | 1.2% | 1.7% | 2.9% | 2.5% |
| CO, CO2 | 3.1% | 3.7% | 4.3% | 5% |

Four weight checks were performed on all product streams to compile a net yield profile. The net yield profile was an average of the weight checks. Table 9 summarizes the carbon yield profile for the Xylenes-SAK configuration and compares the carbon yield profile to the HAU configuration, NBX configuration, and the baseline configuration. Carbon that was once sequestered by $C_{10+}$ aromatics and PNAs (e.g., napthalenes) was redistributed into higher value products including saturated compounds like paraffins and naphthenes, as well as unsaturated compounds like aromatics and olefins.

Thus, the present disclosure provides systems and methods for shifting the yield structure of hydrocarbon feeds from non-aromatic compounds (e.g., paraffins, napthenes to $C_{6-10}$ aromatic compounds). In some embodiments, the present disclosure provides systems and methods for upgrading light hydrocarbon streams (e.g., $C_{5-}$) and heavy hydrocarbon streams (e.g., $C_{11+}$) within the hydrocarbon feed to increase the yield of aromatic compounds (e.g., $C_{6-10}$), particularly benzene, toluene, para-xylene, ortho-xylene, and meta-xylene.

Although the invention has been described in considerable detail with reference to certain embodiments, one skilled in the art will appreciate that the present invention can be used in alternative embodiments to those described, which have been presented for purposes of illustration and not of limitation. Therefore, the scope of the appended claims should not be limited to the description of the embodiments contained herein.

For reasons of completeness, various aspects of the invention are set out in the following numbered clauses:

Clause 1. A process for producing and separating aromatic hydrocarbons from a hydrocarbon feed stream, the hydrocarbon feed stream comprising a plurality of non-aromatic hydrocarbons and aromatic hydrocarbons, wherein the non-aromatic hydrocarbons comprise one or more of a paraffin, an olefin, a napthene, or combinations thereof, and wherein the aromatic compounds includes one or more of an aryl, a fused aryl, a polycylic compound, or combinations thereof, the process comprising:

(i) fractionating, using a series of distillation columns, the hydrocarbon feed stream to separate an aromatics product stream and a heavy hydrocarbon stream from the hydrocarbon feed stream, wherein the aromatics product stream comprises at least one of a $C_6$ aromatic, a $C_7$ aromatic, a $C_8$ aromatic, or a combination thereof, and wherein the heavy hydrocarbon stream comprises $C_{11+}$ compounds;

(ii) contacting the heavy hydrocarbon stream with a hydrogenation catalyst in the presence of hydrogen to produce a hydrogenated $C_{11+}$ stream; and (iii) contacting the hydrogenated $C_{11+}$ stream with the least one conversion catalyst to dealkylate at least a portion of the $C_{11+}$ compounds to generate a reformate stream, wherein the reformate stream is fed to the series of distillation columns of step (i).

Clause 2. The process of clause 1, wherein step (i) further comprises:
fractionating, using a first distillation column, the hydrocarbon feed stream to separate a $C_{5-}$ stream and a $C_{6+}$ stream from the hydrocarbon feed stream;
fractionating, using a second distillation column, the $C_{6+}$ stream into the aromatic product stream and a $C_{9+}$ stream, wherein the aromatic product stream comprises $C_{6-8}$ compounds; and fractionating, using a third distillation column, the $C_{9+}$ stream into a $C_{9-10}$ stream and the heavy hydrocarbon stream.

Clause 3. The process of clause 2 further comprising:
recycling the $C_{5-}$ stream to the at least one conversion catalyst.

Clause 4. The process of clause 2, wherein the $C_{6-8}$ stream comprises at least one of benzene, toluene, xylenes, or a combination thereof.

Clause 5. The process of clause 1, wherein step (i) further comprises
fractionating, using a first distillation column, the hydrocarbon feed stream to separate a $C_{7-}$ stream and a $C_{8+}$ stream from the hydrocarbon feed stream;
fractionating, using a second distillation column, the $C_{8+}$ stream into the aromatic product stream and a $C_{9+}$ stream, wherein the aromatic product stream comprises $C_8$ compounds; and
fractionating, using a third distillation column, the $C_{9+}$ stream into a $C_{9-10}$ stream and the hydrocarbon stream.

Clause 6. The process of clause 5 further comprising:
recycling the $C_{7-}$ stream to the at least one conversion catalyst.

Clause 7. The process of clause 5 further comprising:
recycling the $C_{9-10}$ stream to the at least one conversion catalyst to dealkylate at least a portion of the $C_{9-10}$ compounds.

Clause 8. The process of clause 1, wherein the hydrogenation catalyst comprises at least one support and at least one metal.

Clause 9. The process of clause 8, wherein the at least one support comprises at least one of carbon, silica, alumina, zirconia, titania, vanadia, ceria, silica-aluminate, zeolite, kieselguhr, hydroxyapatite, zinc oxide, chromia, and combinations thereof.

Clause 10. The process of clause 8, wherein the metal comprises at least one of Fe, Ru, Co, Pt, Pd, Ni, Re, Cu, alloys thereof, and a combination thereof.

Clause 11. The process of clause 8, wherein the hydrogenation catalyst further comprises at least one promoter.

Clause 12. The process of clause 11, wherein the promoter comprises at least one of Ag, Au, Cr, Zn, Mn, Mg, Ca, Cr, Sn, Bi, Mo, W, B, P, and alloys or combinations thereof.

Clause 13. The process of clause 1, wherein the conversion catalyst comprises at least one of carbide, nitride, zirconia, alumina, silica, aluminosilicate, phosphate, zeolite, titanium oxide, zinc oxide, vanadium oxide, lanthanum oxide, yttrium oxide, scandium oxide, magnesium oxide, cerium oxide, barium oxide, calcium oxide, hydroxide, heteropolyacid, inorganic acid, acid modified resin, base modified resin, and combinations thereof.

Clause 14. The process of clause 1, wherein the conversion catalyst comprises at least one metal, wherein the metal comprises at least one of Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof.

Clause 15. The process of clause 1, wherein the conversion catalyst comprises at least one modifier, wherein the modifier comprises at least one of Ce, La, Y, Sc, P, B, Bi, Li, Na, K, Rb, Cs, Mg, Ca, Sr, Ba, and combinations thereof.

Clause 16. The process of clause 1, wherein heavy hydrocarbon stream in step (ii) comprises at least one polynuclear aromatic (PNA), and wherein the conversion of the PNA during hydrogenation is at least 70%, or at least 75%, or at least 80%, or at least 85%, or at least 90%.

Clause 17. The process of clause 1, wherein the hydrogenated $C_{11+}$ stream comprises less than 5 wt % polynuclear aromatic compounds, or less than 4 wt %, or less than 3 wt %, or less than 2 wt %, or less than 1 wt %, based on the total weight of the hydrogenated $C_{11+}$ stream.

Clause 18. The process of clause 1, wherein the hydrogenated $C_{11+}$ stream comprises tetralin, and wherein the hydrogenated $C_{11+}$ stream comprises a weight fraction of tetralin that is at least 10 wt % greater relative to the weight fraction of tetralins in the $C_{11+}$ stream, or at least 20 wt % greater, or at least 30 wt % greater, or at least 40 wt % greater, or at least 50 wt % greater, based on the total weight of the respective streams.

Clause 19. The process of clause 1, wherein the hydrogenated $C_{11+}$ stream comprises decalin, and wherein the hydrogenated $C_{11+}$ stream comprises a weight fraction of tetralin that is at least 10 wt % greater relative to the weight fraction of tetralins in the $C_{11+}$ stream, or at least 20 wt % greater, or at least 30 wt % greater, or at least 40 wt % greater, or at least 50 wt % greater, based on the total weight of the respective streams.

Clause 20. The process of clause 1, wherein prior to step (i) the method further comprises:
catalytically reacting a feedstock stream comprising water and oxygenated hydrocarbons in the presence of hydrogen with a deoxygenation catalyst to produce a deoxygenated product stream; and
catalytically reacting the deoxygenated product stream with the at least one conversion catalyst to produce the hydrocarbon feed stream.

Clause 21. A process comprising:
(i) catalytically reacting a feedstock stream comprising water and oxygenated hydrocarbons in the presence of hydrogen with a deoxygenation catalyst to produce a deoxygenated product stream;
(ii) catalytically reacting the deoxygenated product stream with the at least one conversion catalyst to produce a condensation product stream comprising non-aromatic hydrocarbons and aromatic hydrocarbons, wherein the non-aromatic hydrocarbons comprise one or more of a paraffin, an olefin, a napthene, or combinations thereof, and wherein the aromatic compounds includes one or more of an aryl, a fused aryl, a polycylic compound, or combinations thereof;
(iii) fractionating, using a series of distillation columns, the condensation product stream to separate an aromatics product stream and a heavy hydrocarbon stream from the condensation product stream, wherein the aromatics product stream comprises at least one of a $C_6$ aromatic, a $C_7$ aromatic, a $C_8$ aromatic, or a combination thereof, and wherein the heavy hydrocarbon stream comprises $C_{11+}$ compounds; and
(iv) recycling at least a portion of the heavy hydrocarbon stream to the deoxygenation catalyst of step (i).

Clause 22. The process of clause 21, wherein the oxygenated hydrocarbons comprise one or more of a monosaccharide, a disaccharide, a oligosaccharide, a polysaccharide, a sugar alcohol, a sugar degradation product, a cellulosic derivative, a hemicellulosic derivative, a lignin derivative, a lingnocellulosic derivative, and a combination thereof.

Clause 23. The process of clause 21, wherein step (iii) further comprises:
fractionating, using a first distillation column, the condensation stream to separate a $C_{5-}$ stream and a $C_{6+}$ stream from the condensation stream;
fractionating, using a second distillation column, the $C_{6+}$ stream into the aromatic product stream and a $C_{9+}$ stream, wherein the aromatic product stream comprises $C_{6-8}$ compounds; and
fractionating, using a third distillation column, the $C_{9+}$ stream into a $C_{9-10}$ stream and the heavy hydrocarbon stream.

Clause 24. The process of clause 23 further comprising:
contacting the $C_{5-}$ stream with the at least one conversion catalyst to convert at least a portion of $C_{5-}$ compounds into $C_{4+}$ compounds via condensation reactions.

Clause 25. The process of clause 23, wherein the $C_{6-8}$ stream comprises at least one of benzene, toluene, xylenes, or a combination thereof.

Clause 26. The process of clause 21, wherein step (iii) further comprises
fractionating, using a first distillation column, the condensation stream to separate a $C_{7-}$ stream and a $C_{8+}$ stream from the condensation stream;
fractionating, using a second distillation column, the $C_{8+}$ stream into the aromatic product stream and a $C_{9+}$ stream, wherein the aromatic product stream comprises $C_8$ compounds; and
fractionating, using a third distillation column, the $C_{9+}$ stream into a $C_{9-10}$ stream and the heavy hydrocarbon stream.

Clause 27. The process of clause 26 further comprising:
contacting the $C_{7-}$ stream with the at least one conversion catalyst to convert at least a portion of $C_{7-}$ compounds into $C_{4+}$ compounds via condensation reactions.

Clause 28. The process of clause 26 further comprising:
contacting the $C_{9-10}$ stream with the at least one conversion catalyst to dealkylate at least a portion of the $C_{9-10}$ compounds.

Clause 29. The process of clause 21, wherein the deoxygenation catalyst comprises at least one support and at least one metal.

Clause 30. The process of clause 29, wherein the at least one support comprises zirconia.

Clause 31. The process of clause 29, wherein the at least one metal comprises Pd, W, or a combination thereof.

Clause 32. The process of clause 29, wherein the deoxygenation catalyst comprises a promoter.

Clause 33. The process of clause 32, wherein the promoter comprises Sn, W, or a combination thereof.

Clause 34. The process of clause 21, wherein the conversion catalyst comprises a zeolite.

Clause 35. The process of clause 21, wherein the conversion catalyst comprises at least one metal.

Clause 36. The process of clause 35, wherein the metal is Ni.

The invention claimed is:

1. A process for producing and separating aromatic hydrocarbons from a hydrocarbon feed stream, the hydrocarbon feed stream comprising a plurality of non-aromatic hydrocarbons and aromatic hydrocarbons, wherein the non-aromatic hydrocarbons comprise a paraffin, an olefin, a naphthene, or a combination thereof, and wherein the aromatic hydrocarbons comprise an aryl, a fused aryl, a polycylic compound, or a combination thereof, the process comprising:
   (i) fractionating, using a series of distillation columns, the hydrocarbon feed stream to separate an aromatics product stream and a heavy hydrocarbon stream from the hydrocarbon feed stream, wherein the aromatics product stream comprises a $C_6$ aromatic, a $C_7$ aromatic, a $C_8$ aromatic, or a combination thereof, and wherein the heavy hydrocarbon stream comprises $C_{11+}$ compounds;
   (ii) contacting the heavy hydrocarbon stream with a hydrogenation catalyst in the presence of hydrogen to produce a hydrogenated $C_{11+}$ stream; and
   (iii) contacting the hydrogenated $C_{11+}$ stream with at least one conversion catalyst to dealkylate at least a portion of the $C_{11+}$ compounds to generate a reformate stream, wherein the reformate stream is fed to the series of distillation columns of step (i).

2. The process of claim 1, wherein step (i) further comprises:
   fractionating, using a first distillation column, the hydrocarbon feed stream to separate a $C_{5-}$ stream and a $C_{6+}$ stream from the hydrocarbon feed stream;
   fractionating, using a second distillation column, the $C_{6+}$ stream into the aromatic product stream and a $C_{9+}$ stream, wherein the aromatic product stream comprises $C_{6-8}$ compounds; and
   fractionating, using a third distillation column, the $C_{9+}$ stream into a $C_{9-10}$ stream and the heavy hydrocarbon stream.

3. The process of claim 2 further comprising:
   recycling the $C_{5-}$ stream to the at least one conversion catalyst.

4. The process of claim 1, wherein step (i) further comprises
   fractionating, using a first distillation column, the hydrocarbon feed stream to separate a $C_{7-}$ stream and a $C_{8+}$ stream from the hydrocarbon feed stream;
   fractionating, using a second distillation column, the $C_{8+}$ stream into the aromatic product stream and a $C_{9+}$ stream, wherein the aromatic product stream comprises $C_8$ compounds; and
   fractionating, using a third distillation column, the $C_{9+}$ stream into a $C_{9-10}$ stream and the heavy hydrocarbon stream.

5. The process of claim 4 further comprising:
   recycling the $C_{7-}$ stream to the at least one conversion catalyst.

6. The process of claim 4 further comprising:
   recycling the $C_{9-10}$ stream to the at least one conversion catalyst to dealkylate at least a portion of $C_{9-10}$ compounds in the $C_{9-10}$ stream.

7. The process of claim 1, wherein the hydrogenation catalyst comprises at least one support and at least one metal;
   wherein the at least one support comprises at least one of carbon, silica, alumina, zirconia, titania, vanadia, ceria, silica-aluminate, zeolite, kieselguhr, hydroxyapatite, zinc oxide, chromia, and combinations thereof, and
   wherein the at least one metal comprises Fe, Ru, Co, Pt, Pd, Ni, Re, Cu, alloys thereof, or a combination thereof.

8. The process of claim 1, wherein the conversion catalyst comprises:
   a zeolite; and
   at least one metal, wherein the metal comprises Cu, Ag, Au, Pt, Ni, Fe, Co, Ru, Zn, Cd, Ga, In, Rh, Pd, Ir, Re, Mn, Cr, Mo, W, Sn, Os, alloys, or a combination thereof.

9. The process of claim 1, wherein the heavy hydrocarbon stream in step (ii) comprises at least one polynuclear aromatic (PNA), and wherein the conversion of the PNA during hydrogenation is at least 70%.

10. The process of claim 1, wherein the hydrogenated $C_{11+}$ stream comprises less than 5 wt % polynuclear aromatic compounds, based on the total weight of the hydrogenated $C_{11+}$ stream.

11. The process of claim 1, wherein the hydrogenated $C_{11+}$ stream comprises tetralins, and wherein the hydrogenated $C_{11+}$ stream comprises a weight fraction of tetralins that is at least 10 wt % greater relative to the weight fraction of tetralins in the heavy hydrocarbon stream comprising $C_{11+}$ compounds, based on the total weight of the respective streams.

12. The process of claim 1, wherein the hydrogenated $C_{11+}$ stream comprises decalins, and wherein the hydrogenated $C_{11+}$ stream comprises a weight fraction of decalins that is at least 10 wt % greater relative to the weight fraction of decalins in the heavy hydrocarbon stream comprising $C_{11+}$ compounds, based on the total weight of the respective streams.

13. The process of claim 1, wherein prior to step (i) the method further comprises:
   catalytically reacting a feedstock stream comprising water and oxygenated hydrocarbons in the presence of hydrogen with a deoxygenation catalyst to produce a deoxygenated product stream; and
   catalytically reacting the deoxygenated product stream with the at least one conversion catalyst to produce the hydrocarbon feed stream.

* * * * *